US012738354B2

(12) United States Patent
Subramanian

(10) Patent No.: US 12,738,354 B2
(45) Date of Patent: Sep. 15, 2026

(54) MACHINE LEARNING MODELS FOR AUTOMATED ENTITY FIELD CORRECTION

(71) Applicant: Express Scripts Strategic Development, Inc., St. Louis, MO (US)

(72) Inventor: Viswanathan Subramanian, Edison, NJ (US)

(73) Assignee: Express Scripts Strategic Development, Inc., St. Louis, MO (US)

( * ) Notice: Subject to any disclaimer, the term of this patent is extended or adjusted under 35 U.S.C. 154(b) by 247 days.

(21) Appl. No.: 17/992,347

(22) Filed: Nov. 22, 2022

(65) Prior Publication Data

US 2023/0162831 A1 May 25, 2023

Related U.S. Application Data

(63) Continuation-in-part of application No. 17/576,055, filed on Jan. 14, 2022.

(60) Provisional application No. 63/282,208, filed on Nov. 23, 2021.

(51) Int. Cl.
*G16H 20/10* (2018.01)
*G16H 10/60* (2018.01)

(52) U.S. Cl.
CPC ............. *G16H 20/10* (2018.01); *G16H 10/60* (2018.01)

(58) Field of Classification Search
CPC ............................... G16H 20/10; G16H 10/60
USPC ............................................................. 705/3
See application file for complete search history.

(56) References Cited

U.S. PATENT DOCUMENTS

| | | | |
|---|---|---|---|
| 8,566,121 | B2 | 10/2013 | Ramasubramanian |
| 9,720,954 | B2 | 8/2017 | Wilding |
| 9,727,598 | B2 | 8/2017 | Wilding |
| 9,940,452 | B2 | 4/2018 | Chen |
| 10,061,763 | B2 | 8/2018 | Tamilarasan |
| 10,089,473 | B2 | 10/2018 | Mahrous |

(Continued)

OTHER PUBLICATIONS

Emmanuel, T., Maupong, T., Mpoeleng, D. et al. A survey on missing data in machine learning. J Big Data 8, 140 (2021). https://doi.org/10.1186/s40537-021-00516-9, Accepted Sep. 12, 2021, Published Oct. 27, 2021, downloaded Oct. 23, 2024 (Year: 2021).*

(Continued)

*Primary Examiner* — Scott D Gartland
(74) *Attorney, Agent, or Firm* — Harness IP

(57) ABSTRACT

A method for automated entity field correction includes scanning a database entity to generate structured scan data, generating a feature vector input according to the structured scan data, and processing, by a machine learning model, the feature vector input to generate an entity field output including multiple identified entity fields and values of the identified entity fields. In response to determining that the entity field output includes at least one missing field value, the method includes accessing a record database to identify a predicted value for the missing field value, comparing a predicted name string of the predicted value to a scanned name string of the structured scan data to determine at least one of a Levenshtein distance and a Jaro-Winkler distance, and transmitting the database entity to a prescription fill processing module for automated processing of a prescription fill specified by the database entity.

20 Claims, 16 Drawing Sheets

ARTworks control number: 3278347 Patient Name: John Smith Age: 42 DOB:2/10/1980 Address: 123 Clinton Ave, Houston, TX 83232 Patient Home Phone: 8239232244 Allergies: RX Substitutions allowed Date Prescribed: 05/06/2019 Start Date: 05/07/2019 Sharps container Progesterone in oil 50mg/ml #3 10ml vials; # 30 3cc syringes with 18g 1 1/2needles; # 30 22g 1 1/2 needles only 1m| IM QD when directed (with a range of 25-100 mg daily) with 3 refills RX Special Instructions: None Ordering physician: Osheroff, Joseph, MD DEA #: BO4507779 Physician Address Columbia OFC SGF 10630 LITTLE PATUXENT PARKWAY, CENTURY PLAZA 1000 SUITE 305 COLUMBIA, MD 21044 (410) 997-6999 Electronically signed by: Osheroff, Joseph, MD The following prescription is being electronically transmitted to Freedom Fertility Pharmacy e-Prescription

1202

1204

Entity Field Recognition

ARTworks control number: 3278347 Patient Name: John Smith Age: 42 DOB:2/10/1980 Address: 123 Clinton Ave, Houston, TX 83232 Patient Home Phone: 8239232244 Allergies: RX Substitutions allowed Date Prescribed: 05/06/2019 Start Date: 05/07/2019 Sharps container Progesterone in oil 50mg/ml #3 10ml vials; # 30 3cc syringes with 18g 1 1/2needles; # 30 22g 1 1/2 needles only 1m| IM QD when directed (with a range of 25-100 mg daily) with 3 refills RX Special Instructions: None Ordering physician: Osheroff, Joseph, MD DEA #: BO4507779 Physician Address Columbia OFC SGF 10630 LITTLE PATUXENT, CENTURY PLAZA 1000 SUITE 305 COLUMBIA, MD 21044 (410) 997-6999 Electronically signed by: Osheroff, Joseph, MD The following prescription is being electronically transmitted to Freedom Fertility Pharmacy e-Prescription

(56) References Cited

U.S. PATENT DOCUMENTS

| | | | | |
|---|---|---|---|---|
| 10,235,633 | B2 | 3/2019 | Tereshkov | |
| 10,242,258 | B2 | 3/2019 | Guo | |
| 10,262,112 | B2 | 4/2019 | Ryan | |
| 10,375,105 | B2 | 8/2019 | Kozloski | |
| 10,482,323 | B2 | 11/2019 | Saxena | |
| 10,649,972 | B2 | 5/2020 | Lima | |
| 10,776,796 | B2 | 9/2020 | Amarthaluri | |
| 10,860,557 | B2 | 12/2020 | Eberl | |
| 10,984,340 | B2 | 4/2021 | Hsiao | |
| 11,417,421 | B1 * | 8/2022 | Tate | G16H 10/60 |
| 2003/0158755 | A1 | 8/2003 | Neuman | |
| 2008/0208655 | A1 | 8/2008 | Russo | |
| 2010/0324936 | A1 | 12/2010 | Vishnubhatla | |
| 2011/0295621 | A1 | 12/2011 | Farooq | |
| 2012/0191502 | A1 | 7/2012 | Gross | |
| 2013/0226967 | A1 | 8/2013 | Gross | |
| 2014/0052688 | A1 | 2/2014 | Bansal | |
| 2014/0081652 | A1 | 3/2014 | Klindworth | |
| 2014/0095201 | A1 | 4/2014 | Farooq | |
| 2014/0257832 | A1 | 9/2014 | Hermiz | |
| 2014/0278466 | A1 * | 9/2014 | Simmons | G16H 20/10 705/2 |
| 2016/0117471 | A1 | 4/2016 | Belt | |
| 2018/0315055 | A1 | 11/2018 | Pickover | |
| 2018/0322597 | A1 | 11/2018 | Sher | |
| 2020/0227147 | A1 | 7/2020 | Raddatz | |
| 2020/0257963 | A1 | 8/2020 | Abhinav | |
| 2020/0364243 | A1 * | 11/2020 | Tamayo-Rios | G06F 16/2458 |
| 2022/0351842 | A1 * | 11/2022 | Zheng | G16H 50/20 |

OTHER PUBLICATIONS

Robinson et al., Data Structure definition, from Tech Target, downloaded from https://www.techtarget.com/searchdatamanagement/definition/data-structure#:~:text=A%20data%20structure%20is%20a,to%20suit%20a%20specific%20purpose. on Oct. 22, 2024 (Year: 2024).*

Alhorishi et al., Using Machine Learning to Predict Early Preparation of Pharmacy Prescriptions at PSMMC—a Comparison of Four Machine Learning Algorithms. Acta Inform Med. Mar. 2021;29(1):21-25. doi: 10.5455/aim.2021.29.21-25. PMID: 34012209; PMCID: PMC8116105. Downloaded Sep. 23, 2024 (Year: 2021).*

Ngiam, Kee Yuan et al., Big data and machine learning algorithms for health-care delivery, The Lancet Oncology, vol. 20, Iss. 5, e262-e273, May 2019, DOI: 10.1016/S1470-2045(19)30149-4, downloaded Oct. 23, 2024 (Year: 2019).*

Hassan et al., "Medical Prescription Recognition using Machine Learning," 2021 IEEE 11th Annual Computing and Communication Workshop and Conference (CCWC), NV, USA, 2021, pp. 0973-0979, doi: 10.1109/CCWC51732.2021.9376141 (Year: 2021).*

Google Search Results for "automated measuring sealing pharmaceutical container"—screenshots of the first and second results groupings—search limited to being before Nov. 22, 2022, results from Sep. 6, 2025 search (Year: 2022).*

Zahray, Lisa, Automating Data Extraction from Prescription Document Images to Reduce Human Error, MIT Dept. of Elect. Eng. and Computer Science, published Jun. 2019, downloaded Mar. 2, 2026 from https://dspace.mit.edu/bitstream/handle/1721.1/128575/1220877663-MIT.pdf?sequence=1&isAllowed=y (Year: 2019).*

* cited by examiner

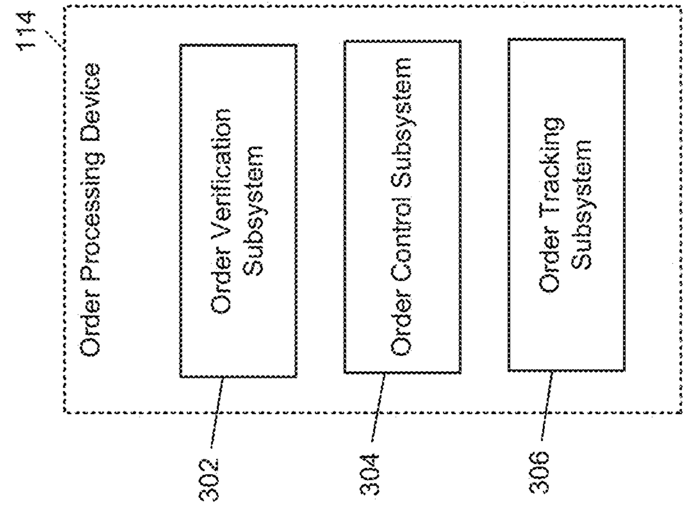
FIG. 3

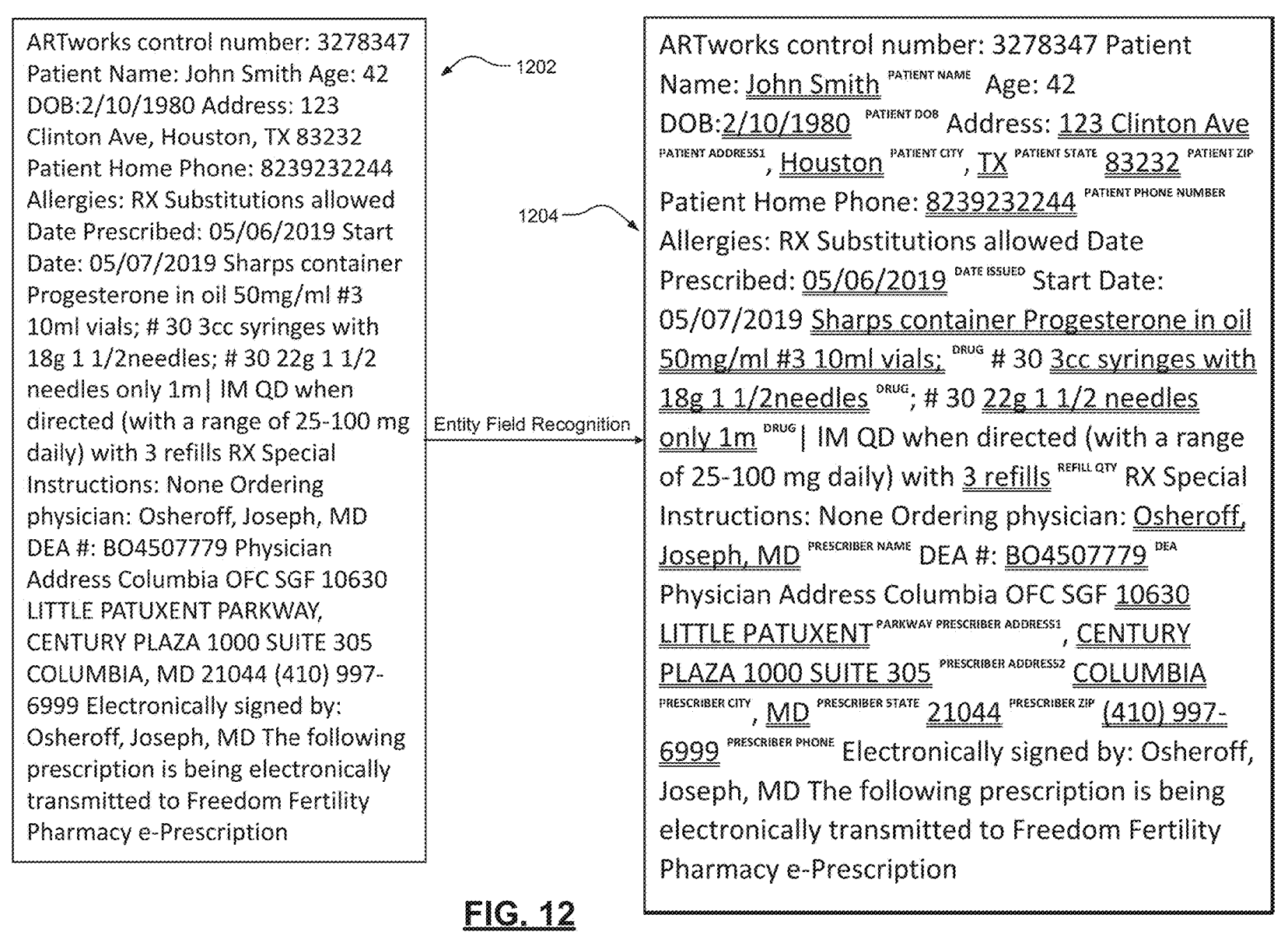

1202

ARTworks control number: 3278347 Patient Name: John Smith Age: 42 DOB:2/10/1980 Address: 123 Clinton Ave, Houston, TX 83232 Patient Home Phone: 8239232244 Allergies: RX Substitutions allowed Date Prescribed: 05/06/2019 Start Date: 05/07/2019 Sharps container Progesterone in oil 50mg/ml #3 10ml vials; # 30 3cc syringes with 18g 1 1/2needles; # 30 22g 1 1/2 needles only 1m| IM QD when directed (with a range of 25-100 mg daily) with 3 refills RX Special Instructions: None Ordering physician: Osheroff, Joseph, MD DEA #: BO4507779 Physician Address Columbia OFC SGF 10630 LITTLE PATUXENT PARKWAY, CENTURY PLAZA 1000 SUITE 305 COLUMBIA, MD 21044 (410) 997-6999 Electronically signed by: Osheroff, Joseph, MD The following prescription is being electronically transmitted to Freedom Fertility Pharmacy e-Prescription Entity Field Recognition

1204

ARTworks control number: 3278347 Patient Name: John Smith PATIENT NAME Age: 42 DOB:2/10/1980 PATIENT DOB Address: 123 Clinton Ave PATIENT ADDRESS1 , Houston PATIENT CITY , TX PATIENT STATE 83232 PATIENT ZIP Patient Home Phone: 8239232244 PATIENT PHONE NUMBER Allergies: RX Substitutions allowed Date Prescribed: 05/06/2019 DATE ISSUED Start Date: 05/07/2019 Sharps container Progesterone in oil 50mg/ml #3 10ml vials; DRUG # 30 3cc syringes with 18g 1 1/2needles DRUG; # 30 22g 1 1/2 needles only 1m DRUG | IM QD when directed (with a range of 25-100 mg daily) with 3 refills REFILL QTY RX Special Instructions: None Ordering physician: Osheroff, Joseph, MD PRESCRIBER NAME DEA #: BO4507779 DEA Physician Address Columbia OFC SGF 10630 LITTLE PATUXENT PARKWAY PRESCRIBER ADDRESS1 , CENTURY PLAZA 1000 SUITE 305 PRESCRIBER ADDRESS2 COLUMBIA PRESCRIBER CITY , MD PRESCRIBER STATE 21044 PRESCRIBER ZIP (410) 997-6999 PRESCRIBER PHONE Electronically signed by: Osheroff, Joseph, MD The following prescription is being electronically transmitted to Freedom Fertility Pharmacy e-Prescription

FIG. 12

MACHINE LEARNING MODELS FOR AUTOMATED ENTITY FIELD CORRECTION

CROSS-REFERENCE TO RELATED APPLICATIONS

This application is a continuation-in-part of U.S. patent application Ser. No. 17/576,055, filed on Jan. 14, 2022. This application claims the benefit and priority of U.S. Provisional Application No. 63/282,208, filed on Nov. 23, 2021. The entire disclosures of each of the above applications are incorporated herein by reference.

FIELD

The present disclosure relates to machine learning models for automated entity field correction.

BACKGROUND

Prescribers submit prescription fill requests for filling by pharmacies in a variety of formats, including electronic requests and faxed request documents. With electronic requests (such as eRx submissions), each data element is clearly identified using standardized field labels and data formats. Fax documents do not include standardized electronic field labels for different data fields, so a system must identify necessary data elements needed for processing of a fill request. Fax documents use many different formats and layouts, so it is not possible to use a single blueprint that specifies an exact location of each data field for all fax document formats.

The background description provided here is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

A computer system includes memory hardware configured to store a machine learning model, a record database, and computer-executable instructions, wherein the record database includes multiple patient data structures and multiple prescriber data structures. The system includes processor hardware configured to execute the instructions, wherein the instructions include scanning a database entity to generate structured scan data specific to the database entity, generating a feature vector input according to the structured scan data, processing, by the machine learning model, the feature vector input to generate an entity field output including multiple identified entity fields and values of the identified entity fields, determining whether the entity field output includes at least one missing field value, and transmitting the database entity to a prescription fill processing module for automated processing of a prescription fill specified by the database entity, in response to determining that the entity field output does not include at least one missing field value. In response to determining that the entity field output includes at least one missing field value, the instructions include accessing the record database to identify a predicted value for the at least one missing field value in the entity field output, wherein the predicted value is stored in association with at least one entity field value of the entity field output in at least one of the multiple patient data structures and the multiple prescriber data structures of the record database, comparing a predicted name string of the predicted value to a scanned name string of the structured scan data to determine at least one of a Levenshtein distance and a Jaro-Winkler distance between the predicted name string and the scanned name string, and in response to determining that a similarity score between the predicted name string and the scanned name string according to the at least one of the a Levenshtein distance and the Jaro-Winkler distance is greater than a specified similarity threshold, transmitting the database entity to the prescription fill processing module for automated processing of the prescription fill specified by the database entity.

In other features, comparing the predicted name string to the scanned name string includes determining both of the Levenshtein distance and the Jaro-Winkler distance between the predicted name string and the scanned name string, and the similarity score between the predicted name string and the scanned name string is determined according to both the Levenshtein distance and the Jaro-Winkler distance between the predicted name string and the scanned name string. in other features, the similarity score between the predicted name string and the scanned name string is determined according to both the Levenshtein distance and the Jaro-Winkler distance.

In other features, the memory hardware is configured to store historical feature vector inputs, and the historical feature vector inputs include historical data structures specific to multiple historical database entities, and the instructions include training the machine learning model with the historical feature vector inputs to generate an entity field output, wherein the entity field output includes multiple identified entity fields and values of the identified entity fields. In other features, the instructions include determining whether the predicted value for the at least one missing field value in the entity field output includes a predicted date field, comparing the predicted date field to a scanned date field of the structured scan data, and in response to determining that the predicted date field to a scanned date field of the structured scan data, transmitting the database entity including the predicted date field to the prescription fill processing module.

In other features, the memory hardware is configured to store multiple date field formats, and comparing the predicted date field to the scanned date field includes, for each of the multiple date field formats, determining whether the structured scan data includes a date value having the date field format. In other features, the memory hardware is configured to store structured classification data, wherein the structured classification data includes multiple entity classification types, and the instructions include analyzing the database entity to identify one of the multiple entity classification types corresponding to the database entity.

In other features, the memory hardware is configured to store multiple machine learning models each associated with a different one of the multiple entity classification types, the instructions include selecting one of the multiple machine learning models according to the identified one of the multiple entity classification types, and processing the feature vector input includes processing the feature vector input using the selected one of the multiple machine learning models. In other features, obtaining the database entity includes receiving a prescription fill request document via facsimile transmission. In other features, scanning the database entity includes performing automated optical character recognition on the database entity.

A method for automated entity field correction includes scanning a database entity to generate structured scan data specific to the database entity, generating a feature vector input according to the structured scan data, processing, by a machine learning model, the feature vector input to generate an entity field output including multiple identified entity fields and values of the identified entity fields, determining whether the entity field output includes at least one missing field value, and transmitting the database entity to a prescription fill processing module for automated processing of a prescription fill specified by the database entity, in response to determining that the entity field output does not include at least one missing field value. In response to determining that the entity field output includes at least one missing field value, the method includes accessing a record database to identify a predicted value for the missing field value in the entity field output, wherein the record database includes multiple patient data structures and multiple prescriber data structures, and wherein the predicted value is stored in association with at least one entity field value of the entity field output in at least one of the multiple patient data structures and the multiple prescriber data structures of the record database, comparing a predicted name string of the predicted value to a scanned name string of the structured scan data to determine at least one of a Levenshtein distance and a Jaro-Winkler distance between the predicted name string and the scanned name string, and in response to determining that a similarity score between the predicted name string and the scanned name string according to the at least one of the a Levenshtein distance and the Jaro-Winkler distance is greater than a specified similarity threshold, transmitting the database entity to the prescription fill processing module for automated processing of the prescription fill specified by the database entity.

In other features, comparing the predicted name string to the scanned name string includes determining both of the Levenshtein distance and the Jaro-Winkler distance between the predicted name string and the scanned name string, and the similarity score between the predicted name string and the scanned name string is determined according to both the Levenshtein distance and the Jaro-Winkler distance between the predicted name string and the scanned name string. In other features, the similarity score between the predicted name string and the scanned name string is determined according to both the Levenshtein distance and the Jaro-Winkler distance.

In other features, the method includes training the machine learning model with historical feature vector inputs to generate an entity field output, wherein the historical feature vector inputs include historical data structures specific to multiple historical database entities, and the entity field output includes multiple identified entity fields and values of the identified entity fields. In other features, the method includes determining whether the predicted value for the missing field value in the entity field output includes a predicted date field, comparing the predicted date field to a scanned date field of the structured scan data, and in response to determining that the predicted date field to a scanned date field of the structured scan data, transmitting the database entity including the predicted date field to the prescription fill processing module.

In other features, comparing the predicted date field to the scanned date field includes, for each of multiple date field formats, determining whether the structured scan data includes a date value having the date field format. In other features, the method includes analyzing the database entity to identify one of multiple entity classification types corresponding to the database entity.

In other features, the method includes selecting one of multiple machine learning models according to the identified one of the multiple entity classification types, wherein processing the feature vector input includes processing the feature vector input using the selected one of the multiple machine learning models. In other features, obtaining the database entity includes receiving a prescription fill request document via facsimile transmission. In other features, scanning the database entity includes performing automated optical character recognition on the database entity.

Further areas of applicability of the present disclosure will become apparent from the detailed description, the claims, and the drawings. The detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings.

FIG. 3 is a functional block diagram of an example order processing device, which may be deployed within the system of FIG. 1.

FIG. 12 is a graphical representation of example entity fields in a prescription document.

In the drawings, reference numbers may be reused to identify similar and/or identical elements.

DETAILED DESCRIPTION

High-Volume Pharmacy

Figure 1:
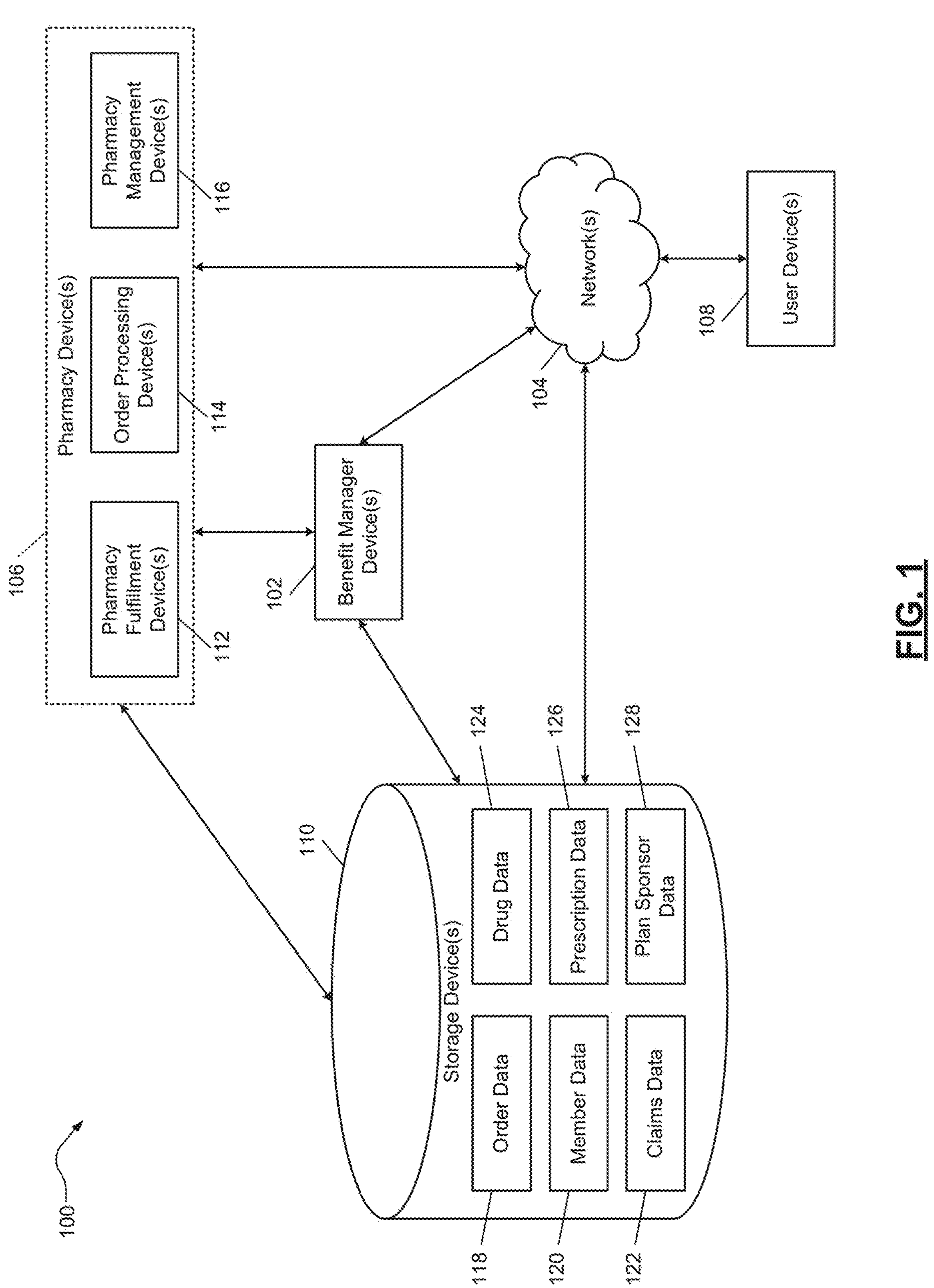
FIG. 1 is a functional block diagram of an example system including a high-volume pharmacy.

FIG. 1 is a block diagram of an example implementation of a system 100 for a high-volume pharmacy. While the system 100 is generally described as being deployed in a high-volume pharmacy or a fulfillment center (for example, a mail order pharmacy, a direct delivery pharmacy, etc.), the system 100 and/or components of the system 100 may otherwise be deployed (for example, in a lower-volume pharmacy, etc.). A high-volume pharmacy may be a pharmacy that is capable of filling at least some prescriptions mechanically. The system 100 may include a benefit manager device 102 and a pharmacy device 106 in communication with each other directly and/or over a network 104.

The system 100 may also include one or more user device(s) 108. A user, such as a pharmacist, patient, data analyst, health plan administrator, etc., may access the benefit manager device 102 or the pharmacy device 106 using the user device 108. The user device 108 may be a desktop computer, a laptop computer, a tablet, a smartphone, etc.

The benefit manager device 102 is a device operated by an entity that is at least partially responsible for creation and/or management of the pharmacy or drug benefit. While the entity operating the benefit manager device 102 is typically a pharmacy benefit manager (PBM), other entities may operate the benefit manager device 102 on behalf of themselves or other entities (such as PBMs). For example, the benefit manager device 102 may be operated by a health plan, a retail pharmacy chain, a drug wholesaler, a data analytics or other type of software-related company, etc. In some implementations, a PBM that provides the pharmacy benefit may provide one or more additional benefits including a medical or health benefit, a dental benefit, a vision benefit, a wellness benefit, a radiology benefit, a pet care benefit, an insurance benefit, a long term care benefit, a nursing home benefit, etc. The PBM may, in addition to its PBM operations, operate one or more pharmacies. The pharmacies may be retail pharmacies, mail order pharmacies, etc.

Some of the operations of the PBM that operates the benefit manager device 102 may include the following activities and processes. A member (or a person on behalf of the member) of a pharmacy benefit plan may obtain a prescription drug at a retail pharmacy location (e.g., a location of a physical store) from a pharmacist or a pharmacist technician. The member may also obtain the prescription drug through mail order drug delivery from a mail order pharmacy location, such as the system 100. In some implementations, the member may obtain the prescription drug directly or indirectly through the use of a machine, such as a kiosk, a vending unit, a mobile electronic device, or a different type of mechanical device, electrical device, electronic communication device, and/or computing device. Such a machine may be filled with the prescription drug in prescription packaging, which may include multiple prescription components, by the system 100. The pharmacy benefit plan is administered by or through the benefit manager device 102.

The member may have a copayment for the prescription drug that reflects an amount of money that the member is responsible to pay the pharmacy for the prescription drug. The money paid by the member to the pharmacy may come from, as examples, personal funds of the member, a health savings account (HSA) of the member or the member's family, a health reimbursement arrangement (HRA) of the member or the member's family, or a flexible spending account (FSA) of the member or the member's family. In some instances, an employer of the member may directly or indirectly fund or reimburse the member for the copayments.

The amount of the copayment required by the member may vary across different pharmacy benefit plans having different plan sponsors or clients and/or for different prescription drugs. The member's copayment may be a flat copayment (in one example, $10), coinsurance (in one example, 10%), and/or a deductible (for example, responsibility for the first $500 of annual prescription drug expense, etc.) for certain prescription drugs, certain types and/or classes of prescription drugs, and/or all prescription drugs. The copayment may be stored in a storage device 110 or determined by the benefit manager device 102.

In some instances, the member may not pay the copayment or may only pay a portion of the copayment for the prescription drug. For example, if a usual and customary cost for a generic version of a prescription drug is $4, and the member's flat copayment is $20 for the prescription drug, the member may only need to pay $4 to receive the prescription drug. In another example involving a worker's compensation claim, no copayment may be due by the member for the prescription drug.

In addition, copayments may also vary based on different delivery channels for the prescription drug. For example, the copayment for receiving the prescription drug from a mail order pharmacy location may be less than the copayment for receiving the prescription drug from a retail pharmacy location.

In conjunction with receiving a copayment (if any) from the member and dispensing the prescription drug to the member, the pharmacy submits a claim to the PBM for the prescription drug. After receiving the claim, the PBM (such as by using the benefit manager device 102) may perform certain adjudication operations including verifying eligibility for the member, identifying/reviewing an applicable formulary for the member to determine any appropriate copayment, coinsurance, and deductible for the prescription drug, and performing a drug utilization review (DUR) for the member. Further, the PBM may provide a response to the pharmacy (for example, the pharmacy system 100) following performance of at least some of the aforementioned operations.

As part of the adjudication, a plan sponsor (or the PBM on behalf of the plan sponsor) ultimately reimburses the pharmacy for filling the prescription drug when the prescription drug is successfully adjudicated. The aforementioned adjudication operations generally occur before the copayment is received and the prescription drug is dispensed. However in some instances, these operations may occur simultaneously, substantially simultaneously, or in a different order. In addition, more or fewer adjudication operations may be performed as at least part of the adjudication process.

The amount of reimbursement paid to the pharmacy by a plan sponsor and/or money paid by the member may be determined at least partially based on types of pharmacy networks in which the pharmacy is included. In some implementations, the amount may also be determined based on other factors. For example, if the member pays the pharmacy for the prescription drug without using the prescription or drug benefit provided by the PBM, the amount of money paid by the member may be higher than when the member uses the prescription or drug benefit. In some implementations, the amount of money received by the pharmacy for dispensing the prescription drug and for the prescription drug itself may be higher than when the member uses the prescription or drug benefit. Some or all of the foregoing operations may be performed by executing instructions stored in the benefit manager device 102 and/or an additional device.

Examples of the network 104 include a Global System for Mobile Communications (GSM) network, a code division multiple access (CDMA) network, 3rd Generation Partnership Project (3GPP), an Internet Protocol (IP) network, a Wireless Application Protocol (WAP) network, or an IEEE 802.11 standards network, as well as various combinations of the above networks. The network 104 may include an optical network. The network 104 may be a local area network or a global communication network, such as the Internet. In some implementations, the network 104 may include a network dedicated to prescription orders: a prescribing network such as the electronic prescribing network operated by Surescripts of Arlington, Virginia.

Moreover, although the system shows a single network 104, multiple networks can be used. The multiple networks may communicate in series and/or parallel with each other to link the devices 102-110.

The pharmacy device 106 may be a device associated with a retail pharmacy location (e.g., an exclusive pharmacy location, a grocery store with a retail pharmacy, or a general sales store with a retail pharmacy) or other type of pharmacy location at which a member attempts to obtain a prescription. The pharmacy may use the pharmacy device 106 to submit the claim to the PBM for adjudication.

Additionally, in some implementations, the pharmacy device 106 may enable information exchange between the pharmacy and the PBM. For example, this may allow the sharing of member information such as drug history that may allow the pharmacy to better service a member (for example, by providing more informed therapy consultation and drug interaction information). In some implementations, the benefit manager device 102 may track prescription drug fulfillment and/or other information for users that are not members, or have not identified themselves as members, at the time (or in conjunction with the time) in which they seek to have a prescription filled at a pharmacy.

The pharmacy device 106 may include a pharmacy fulfillment device 112, an order processing device 114, and a pharmacy management device 116 in communication with each other directly and/or over the network 104. The order processing device 114 may receive information regarding filling prescriptions and may direct an order component to one or more devices of the pharmacy fulfillment device 112 at a pharmacy. The pharmacy fulfillment device 112 may fulfill, dispense, aggregate, and/or pack the order components of the prescription drugs in accordance with one or more prescription orders directed by the order processing device 114.

In general, the order processing device 114 is a device located within or otherwise associated with the pharmacy to enable the pharmacy fulfillment device 112 to fulfill a prescription and dispense prescription drugs. In some implementations, the order processing device 114 may be an external order processing device separate from the pharmacy and in communication with other devices located within the pharmacy.

For example, the external order processing device may communicate with an internal pharmacy order processing device and/or other devices located within the system 100. In some implementations, the external order processing device may have limited functionality (e.g., as operated by a user requesting fulfillment of a prescription drug), while the internal pharmacy order processing device may have greater functionality (e.g., as operated by a pharmacist).

The order processing device 114 may track the prescription order as it is fulfilled by the pharmacy fulfillment device 112. The prescription order may include one or more prescription drugs to be filled by the pharmacy. The order processing device 114 may make pharmacy routing decisions and/or order consolidation decisions for the particular prescription order. The pharmacy routing decisions include what device(s) in the pharmacy are responsible for filling or otherwise handling certain portions of the prescription order. The order consolidation decisions include whether portions of one prescription order or multiple prescription orders should be shipped together for a user or a user family. The order processing device 114 may also track and/or schedule literature or paperwork associated with each prescription order or multiple prescription orders that are being shipped together. In some implementations, the order processing device 114 may operate in combination with the pharmacy management device 116.

The order processing device 114 may include circuitry, a processor, a memory to store data and instructions, and communication functionality. The order processing device 114 is dedicated to performing processes, methods, and/or instructions described in this application. Other types of electronic devices may also be used that are specifically configured to implement the processes, methods, and/or instructions described in further detail below.

In some implementations, at least some functionality of the order processing device 114 may be included in the pharmacy management device 116. The order processing device 114 may be in a client-server relationship with the pharmacy management device 116, in a peer-to-peer relationship with the pharmacy management device 116, or in a different type of relationship with the pharmacy management device 116. The order processing device 114 and/or the pharmacy management device 116 may communicate directly (for example, such as by using a local storage) and/or through the network 104 (such as by using a cloud storage configuration, software as a service, etc.) with the storage device 110.

The storage device 110 may include: non-transitory storage (for example, memory, hard disk, CD-ROM, etc.) in communication with the benefit manager device 102 and/or the pharmacy device 106 directly and/or over the network 104. The non-transitory storage may store order data 118, member data 120, claims data 122, drug data 124, prescription data 126, and/or plan sponsor data 128. Further, the system 100 may include additional devices, which may communicate with each other directly or over the network 104.

The order data 118 may be related to a prescription order. The order data may include type of the prescription drug (for example, drug name and strength) and quantity of the prescription drug. The order data 118 may also include data used for completion of the prescription, such as prescription materials. In general, prescription materials include an electronic copy of information regarding the prescription drug for inclusion with or otherwise in conjunction with the fulfilled prescription. The prescription materials may include electronic information regarding drug interaction warnings, recommended usage, possible side effects, expiration date, date of prescribing, etc. The order data 118 may be used by a high-volume fulfillment center to fulfill a pharmacy order.

In some implementations, the order data 118 includes verification information associated with fulfillment of the prescription in the pharmacy. For example, the order data 118 may include videos and/or images taken of (i) the prescription drug prior to dispensing, during dispensing, and/or after dispensing, (ii) the prescription container (for example, a prescription container and sealing lid, prescription packaging, etc.) used to contain the prescription drug prior to dispensing, during dispensing, and/or after dispensing, (iii) the packaging and/or packaging materials used to ship or otherwise deliver the prescription drug prior to dispensing, during dispensing, and/or after dispensing, and/or (iv) the fulfillment process within the pharmacy. Other types of verification information such as barcode data read from pallets, bins, trays, or carts used to transport prescriptions within the pharmacy may also be stored as order data 118.

The member data 120 includes information regarding the members associated with the PBM. The information stored as member data 120 may include personal information, personal health information, protected health information, etc. Examples of the member data 120 include name, address, telephone number, e-mail address, prescription drug history, etc. The member data 120 may include a plan sponsor identifier that identifies the plan sponsor associated with the member and/or a member identifier that identifies the member to the plan sponsor. The member data 120 may include a member identifier that identifies the plan sponsor associated with the user and/or a user identifier that identifies the user to the plan sponsor. The member data 120 may also include dispensation preferences such as type of label, type of cap, message preferences, language preferences, etc.

The member data 120 may be accessed by various devices in the pharmacy (for example, the high-volume fulfillment center, etc.) to obtain information used for fulfillment and shipping of prescription orders. In some implementations, an external order processing device operated by or on behalf of a member may have access to at least a portion of the member data 120 for review, verification, or other purposes.

In some implementations, the member data 120 may include information for persons who are users of the pharmacy but are not members in the pharmacy benefit plan being provided by the PBM. For example, these users may obtain drugs directly from the pharmacy, through a private label service offered by the pharmacy, the high-volume fulfillment center, or otherwise. In general, the terms "member" and "user" may be used interchangeably.

The claims data 122 includes information regarding pharmacy claims adjudicated by the PBM under a drug benefit program provided by the PBM for one or more plan sponsors. In general, the claims data 122 includes an identification of the client that sponsors the drug benefit program under which the claim is made, and/or the member that purchased the prescription drug giving rise to the claim, the prescription drug that was filled by the pharmacy (e.g., the national drug code number, etc.), the dispensing date, generic indicator, generic product identifier (GPI) number, medication class, the cost of the prescription drug provided under the drug benefit program, the copayment/coinsurance amount, rebate information, and/or member eligibility, etc. Additional information may be included.

In some implementations, other types of claims beyond prescription drug claims may be stored in the claims data 122. For example, medical claims, dental claims, wellness claims, or other types of health-care-related claims for members may be stored as a portion of the claims data 122.

In some implementations, the claims data 122 includes claims that identify the members with whom the claims are associated. Additionally or alternatively, the claims data 122 may include claims that have been de-identified (that is, associated with a unique identifier but not with a particular, identifiable member).

The drug data 124 may include drug name (e.g., technical name and/or common name), other names by which the drug is known, active ingredients, an image of the drug (such as in pill form), etc. The drug data 124 may include information associated with a single medication or multiple medications.

The prescription data 126 may include information regarding prescriptions that may be issued by prescribers on behalf of users, who may be members of the pharmacy benefit plan—for example, to be filled by a pharmacy. Examples of the prescription data 126 include user names, medication or treatment (such as lab tests), dosing information, etc. The prescriptions may include electronic prescriptions or paper prescriptions that have been scanned. In some implementations, the dosing information reflects a frequency of use (e.g., once a day, twice a day, before each meal, etc.) and a duration of use (e.g., a few days, a week, a few weeks, a month, etc.).

In some implementations, the order data 118 may be linked to associated member data 120, claims data 122, drug data 124, and/or prescription data 126.

The plan sponsor data 128 includes information regarding the plan sponsors of the PBM. Examples of the plan sponsor data 128 include company name, company address, contact name, contact telephone number, contact e-mail address, etc.

Figure 2:
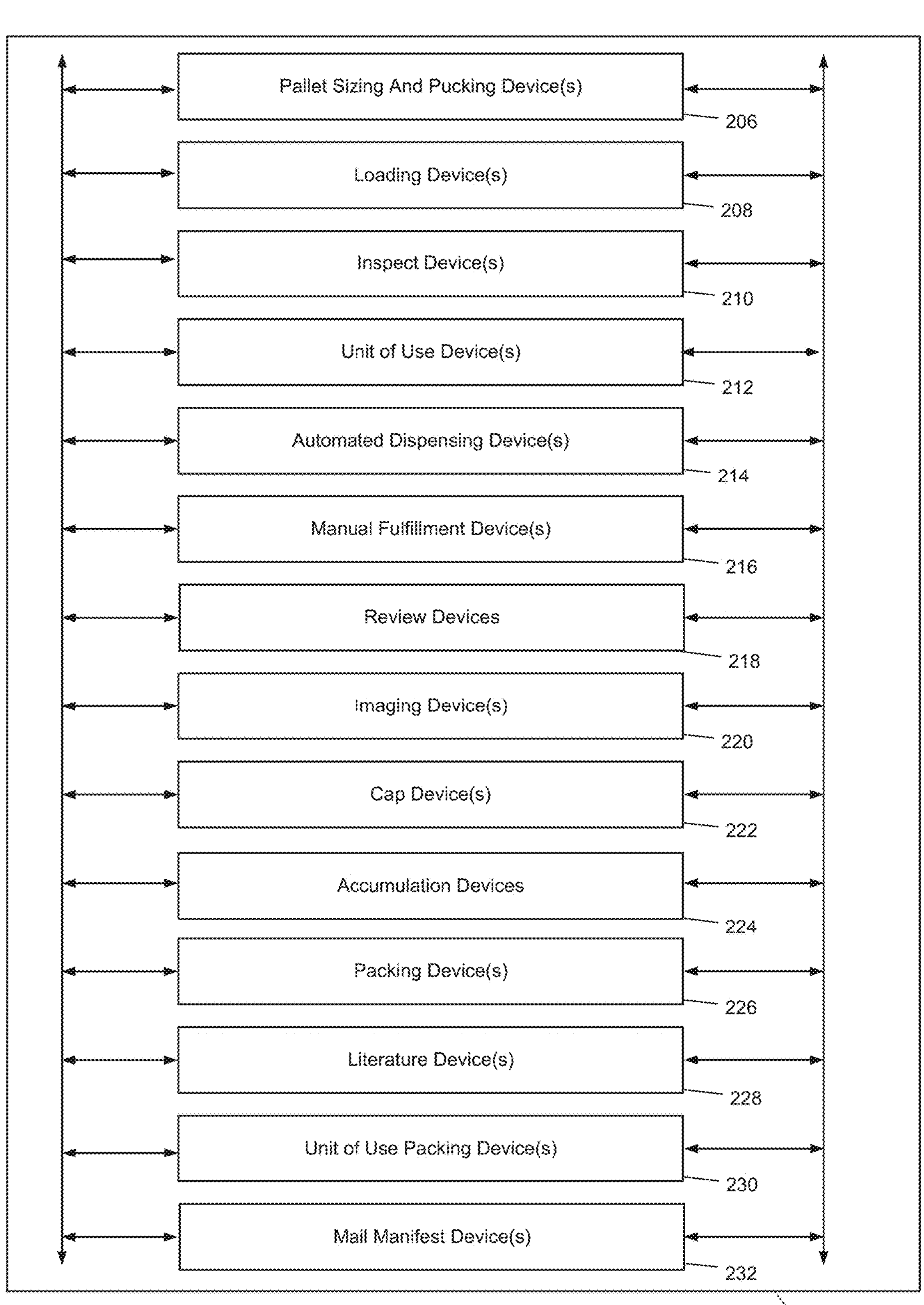
FIG. 2 is a functional block diagram of an example pharmacy fulfillment device, which may be deployed within the system of FIG. 1.

FIG. 2 illustrates the pharmacy fulfillment device 112 according to an example implementation. The pharmacy fulfillment device 112 may be used to process and fulfill prescriptions and prescription orders. After fulfillment, the fulfilled prescriptions are packed for shipping.

The pharmacy fulfillment device 112 may include devices in communication with the benefit manager device 102, the order processing device 114, and/or the storage device 110, directly or over the network 104. Specifically, the pharmacy fulfillment device 112 may include pallet sizing and pucking device(s) 206, loading device(s) 208, inspect device(s) 210, unit of use device(s) 212, automated dispensing device(s) 214, manual fulfillment device(s) 216, review devices 218, imaging device(s) 220, cap device(s) 222, accumulation devices 224, packing device(s) 226, literature device(s) 228, unit of use packing device(s) 230, and mail manifest device(s) 232. Further, the pharmacy fulfillment device 112 may include additional devices, which may communicate with each other directly or over the network 104.

In some implementations, operations performed by one of these devices 206-232 may be performed sequentially, or in parallel with the operations of another device as may be coordinated by the order processing device 114. In some implementations, the order processing device 114 tracks a prescription with the pharmacy based on operations performed by one or more of the devices 206-232.

In some implementations, the pharmacy fulfillment device 112 may transport prescription drug containers, for example, among the devices 206-232 in the high-volume fulfillment center, by use of pallets. The pallet sizing and pucking device 206 may configure pucks in a pallet. A pallet may be a transport structure for a number of prescription containers, and may include a number of cavities. A puck may be placed in one or more than one of the cavities in a pallet by the pallet sizing and pucking device 206. The puck may include a receptacle sized and shaped to receive a prescription container. Such containers may be supported by the pucks during carriage in the pallet. Different pucks may have differently sized and shaped receptacles to accommodate containers of differing sizes, as may be appropriate for different prescriptions.

The arrangement of pucks in a pallet may be determined by the order processing device 114 based on prescriptions that the order processing device 114 decides to launch. The arrangement logic may be implemented directly in the pallet sizing and pucking device 206. Once a prescription is set to be launched, a puck suitable for the appropriate size of container for that prescription may be positioned in a pallet by a robotic arm or pickers. The pallet sizing and pucking device 206 may launch a pallet once pucks have been configured in the pallet.

The loading device 208 may load prescription containers into the pucks on a pallet by a robotic arm, a pick and place mechanism (also referred to as pickers), etc. In various implementations, the loading device 208 has robotic arms or pickers to grasp a prescription container and move it to and from a pallet or a puck. The loading device 208 may also print a label that is appropriate for a container that is to be loaded onto the pallet, and apply the label to the container. The pallet may be located on a conveyor assembly during these operations (e.g., at the high-volume fulfillment center, etc.).

The inspect device 210 may verify that containers in a pallet are correctly labeled and in the correct spot on the pallet. The inspect device 210 may scan the label on one or more containers on the pallet. Labels of containers may be scanned or imaged in full or in part by the inspect device 210. Such imaging may occur after the container has been lifted out of its puck by a robotic arm, picker, etc., or may be otherwise scanned or imaged while retained in the puck. In some implementations, images and/or video captured by the inspect device 210 may be stored in the storage device 110 as order data 118.

The unit of use device 212 may temporarily store, monitor, label, and/or dispense unit of use products. In general, unit of use products are prescription drug products that may be delivered to a user or member without being repackaged at the pharmacy. These products may include pills in a container, pills in a blister pack, inhalers, etc. Prescription drug products dispensed by the unit of use device 212 may be packaged individually or collectively for shipping, or may be shipped in combination with other prescription drugs dispensed by other devices in the high-volume fulfillment center.

At least some of the operations of the devices 206-232 may be directed by the order processing device 114. For example, the manual fulfillment device 216, the review device 218, the automated dispensing device 214, and/or the packing device 226, etc. may receive instructions provided by the order processing device 114.

The automated dispensing device 214 may include one or more devices that dispense prescription drugs or pharmaceuticals into prescription containers in accordance with one or multiple prescription orders. In general, the automated dispensing device 214 may include mechanical and electronic components with, in some implementations, software and/or logic to facilitate pharmaceutical dispensing that would otherwise be performed in a manual fashion by a pharmacist and/or pharmacist technician. For example, the automated dispensing device 214 may include high-volume fillers that fill a number of prescription drug types at a rapid rate and blister pack machines that dispense and pack drugs into a blister pack. Prescription drugs dispensed by the automated dispensing devices 214 may be packaged individually or collectively for shipping, or may be shipped in combination with other prescription drugs dispensed by other devices in the high-volume fulfillment center.

The manual fulfillment device 216 controls how prescriptions are manually fulfilled. For example, the manual fulfillment device 216 may receive or obtain a container and enable fulfillment of the container by a pharmacist or pharmacy technician. In some implementations, the manual fulfillment device 216 provides the filled container to another device in the pharmacy fulfillment devices 112 to be joined with other containers in a prescription order for a user or member.

In general, manual fulfillment may include operations at least partially performed by a pharmacist or a pharmacy technician. For example, a person may retrieve a supply of the prescribed drug, may make an observation, may count out a prescribed quantity of drugs and place them into a prescription container, etc. Some portions of the manual fulfillment process may be automated by use of a machine. For example, counting of capsules, tablets, or pills may be at least partially automated (such as through use of a pill counter). Prescription drugs dispensed by the manual fulfillment device 216 may be packaged individually or collectively for shipping, or may be shipped in combination with other prescription drugs dispensed by other devices in the high-volume fulfillment center.

The review device 218 may process prescription containers to be reviewed by a pharmacist for proper pill count, exception handling, prescription verification, etc. Fulfilled prescriptions may be manually reviewed and/or verified by a pharmacist, as may be required by state or local law. A pharmacist or other licensed pharmacy person who may dispense certain drugs in compliance with local and/or other laws may operate the review device 218 and visually inspect a prescription container that has been filled with a prescription drug. The pharmacist may review, verify, and/or evaluate drug quantity, drug strength, and/or drug interaction concerns, or otherwise perform pharmacist services. The pharmacist may also handle containers which have been flagged as an exception, such as containers with unreadable labels, containers for which the associated prescription order has been canceled, containers with defects, etc. In an example, the manual review can be performed at a manual review station.

The imaging device 220 may image containers once they have been filled with pharmaceuticals. The imaging device 220 may measure a fill height of the pharmaceuticals in the container based on the obtained image to determine if the container is filled to the correct height given the type of pharmaceutical and the number of pills in the prescription. Images of the pills in the container may also be obtained to detect the size of the pills themselves and markings thereon. The images may be transmitted to the order processing device 114 and/or stored in the storage device 110 as part of the order data 118.

The cap device 222 may be used to cap or otherwise seal a prescription container. In some implementations, the cap device 222 may secure a prescription container with a type of cap in accordance with a user preference (e.g., a preference regarding child resistance, etc.), a plan sponsor preference, a prescriber preference, etc. The cap device 222 may also etch a message into the cap, although this process may be performed by a subsequent device in the high-volume fulfillment center.

The accumulation device 224 accumulates various containers of prescription drugs in a prescription order. The accumulation device 224 may accumulate prescription containers from various devices or areas of the pharmacy. For example, the accumulation device 224 may accumulate prescription containers from the unit of use device 212, the automated dispensing device 214, the manual fulfillment device 216, and the review device 218. The accumulation device 224 may be used to group the prescription containers prior to shipment to the member.

The literature device 228 prints, or otherwise generates, literature to include with each prescription drug order. The literature may be printed on multiple sheets of substrates, such as paper, coated paper, printable polymers, or combinations of the above substrates. The literature printed by the literature device 228 may include information required to accompany the prescription drugs included in a prescription order, other information related to prescription drugs in the order, financial information associated with the order (for example, an invoice or an account statement), etc.

In some implementations, the literature device 228 folds or otherwise prepares the literature for inclusion with a prescription drug order (e.g., in a shipping container). In other implementations, the literature device 228 prints the literature and is separate from another device that prepares the printed literature for inclusion with a prescription order.

The packing device 226 packages the prescription order in preparation for shipping the order. The packing device 226 may box, bag, or otherwise package the fulfilled prescription order for delivery. The packing device 226 may further place inserts (e.g., literature or other papers, etc.) into the packaging received from the literature device 228. For example, bulk prescription orders may be shipped in a box, while other prescription orders may be shipped in a bag, which may be a wrap seal bag.

The packing device 226 may label the box or bag with an address and a recipient's name. The label may be printed and affixed to the bag or box, be printed directly onto the bag or box, or otherwise associated with the bag or box. The packing device 226 may sort the box or bag for mailing in an efficient manner (e.g., sort by delivery address, etc.). The packing device 226 may include ice or temperature sensitive elements for prescriptions that are to be kept within a temperature range during shipping (for example, this may be necessary in order to retain efficacy). The ultimate package may then be shipped through postal mail, through a mail order delivery service that ships via ground and/or air (e.g., UPS, FEDEX, or DHL, etc.), through a delivery service, through a locker box at a shipping site (e.g., AMAZON locker or a PO Box, etc.), or otherwise.

The unit of use packing device 230 packages a unit of use prescription order in preparation for shipping the order. The unit of use packing device 230 may include manual scanning of containers to be bagged for shipping to verify each container in the order. In an example implementation, the manual scanning may be performed at a manual scanning station. The pharmacy fulfillment device 112 may also include a mail manifest device 232 to print mailing labels used by the packing device 226 and may print shipping manifests and packing lists.

While the pharmacy fulfillment device 112 in FIG. 2 is shown to include single devices 206-232, multiple devices may be used. When multiple devices are present, the multiple devices may be of the same device type or models, or may be a different device type or model. The types of devices 206-232 shown in FIG. 2 are example devices. In other configurations of the system 100, lesser, additional, or different types of devices may be included.

Moreover, multiple devices may share processing and/or memory resources. The devices 206-232 may be located in the same area or in different locations. For example, the devices 206-232 may be located in a building or set of adjoining buildings. The devices 206-232 may be interconnected (such as by conveyors), networked, and/or otherwise in contact with one another or integrated with one another (e.g., at the high-volume fulfillment center, etc.). In addition, the functionality of a device may be split among a number of discrete devices and/or combined with other devices.

FIG. 3 illustrates the order processing device 114 according to an example implementation. The order processing device 114 may be used by one or more operators to generate prescription orders, make routing decisions, make prescription order consolidation decisions, track literature with the system 100, and/or view order status and other order related information. For example, the prescription order may be comprised of order components.

The order processing device 114 may receive instructions to fulfill an order without operator intervention. An order component may include a prescription drug fulfilled by use of a container through the system 100. The order processing device 114 may include an order verification subsystem 302, an order control subsystem 304, and/or an order tracking subsystem 306. Other subsystems may also be included in the order processing device 114.

The order verification subsystem 302 may communicate with the benefit manager device 102 to verify the eligibility of the member and review the formulary to determine appropriate copayment, coinsurance, and deductible for the prescription drug and/or perform a DUR (drug utilization review). Other communications between the order verification subsystem 302 and the benefit manager device 102 may be performed for a variety of purposes.

The order control subsystem 304 controls various movements of the containers and/or pallets along with various filling functions during their progression through the system 100. In some implementations, the order control subsystem 304 may identify the prescribed drug in one or more than one prescription orders as capable of being fulfilled by the automated dispensing device 214. The order control subsystem 304 may determine which prescriptions are to be launched and may determine that a pallet of automated-fill containers is to be launched.

The order control subsystem 304 may determine that an automated-fill prescription of a specific pharmaceutical is to be launched and may examine a queue of orders awaiting fulfillment for other prescription orders, which will be filled with the same pharmaceutical. The order control subsystem 304 may then launch orders with similar automated-fill pharmaceutical needs together in a pallet to the automated dispensing device 214. As the devices 206-232 may be interconnected by a system of conveyors or other container movement systems, the order control subsystem 304 may control various conveyors: for example, to deliver the pallet from the loading device 208 to the manual fulfillment device 216 from the literature device 228, paperwork as needed to fill the prescription.

The order tracking subsystem 306 may track a prescription order during its progress toward fulfillment. The order tracking subsystem 306 may track, record, and/or update order history, order status, etc. The order tracking subsystem 306 may store data locally (for example, in a memory) or as a portion of the order data 118 stored in the storage device 110.

Automated Entity Field Correction

Figure 4:
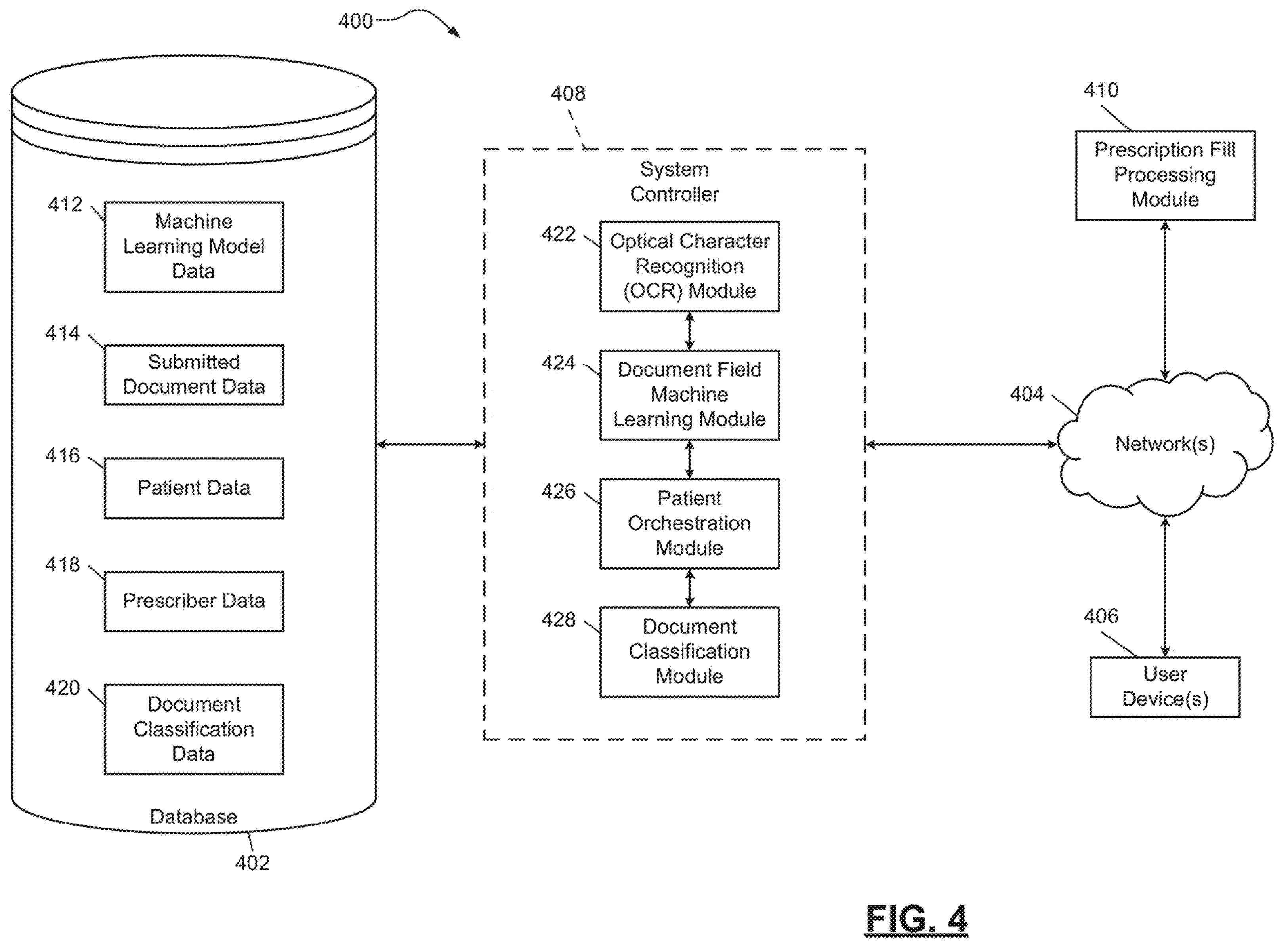
FIG. 4 is a functional block diagram of an example system for automated entity field correction using machine learning models.

FIG. 4 is a functional block diagram of an example system 400 for automated entity field correction using machine learning models, which includes a database 402. While the system 400 is generally described as being deployed in a computer network system, the database 402 and/or components of the system 400 may otherwise be deployed (for example, as a standalone computer setup). The system 400 may include a desktop computer, a laptop computer, a tablet, a smartphone, etc.

As shown in FIG. 4, the database 402 stores machine learning model data 412, submitted document data 414, patient data 416, prescriber data 418, and document classification data 420. In various implementations, the database 402 may store other types of data as well. The machine learning model data 412, submitted document data 414, patient data 416, prescriber data 418, and document classification data 420 may be located in different physical memories within the database 402, such as different random access memory (RAM), read-only memory (ROM), a non-volatile hard disk or flash memory, etc. In some implementations, the machine learning model data 412, submitted document data 414, patient data 416, prescriber data 418, and document classification data 420 may be located in the same memory (such as in different address ranges of the same memory). In various implementations, the machine learning model data 412, submitted document data 414, patient data 416, prescriber data 418, and document classification data 420 may each be stored as structured data in any suitable type of data store.

The machine learning model data 412 may include any suitable data for training one or more machine learning models, such as historical data structures related to one or more of the submitted document data 414, patient data 416, prescriber data 418, and document classification data 420. The machine learning model data 412 may include historical feature vector inputs that are used to train one or more machine learning models to generate a prediction output, such as a prediction of a correct entity field in a document (for example, when a document includes one or more entity fields that are missing data or were not identified when scanning the document with optical character recognition). The historical feature vector inputs may include the historical data structures which are specific to multiple historical database entities (such as multiple historical prescription fill request documents that were received and successfully processed to fill a prescription).

In various implementations, users may train a machine learning model by accessing the system controller 408 via the user device 406. The user device 406 may include any suitable user device for displaying text and receiving input from a user, including a desktop computer, a laptop computer, a tablet, a smartphone, etc. In various implementations, the user device 406 may access the database 402 or the system controller 408 directly, or may access the database 402 or the system controller 408 through one or more networks 404. Example networks may include a wireless network, a local area network (LAN), the Internet, a cellular network, etc.

The system controller 408 may include one or more modules for automated entity field correction. For example, FIG. 4 illustrates an optical character recognition (OCR) module 422, a document field machine learning module 424, a patient orchestration module 426, and a document classification module 428. The OCR module 422 may be configured to perform optical character recognition on documents, such as the submitted document data 414, to automatically identify text and entity fields within the document.

The document field machine learning module may include one or more machine learning models, which may be trained based on, for example, the machine learning model data 412. The document field machine learning module 424 may be trained to automatically process the submitted document data 414, such as by identifying entity fields in scanned text of the submitted document data 414, and predicting values for empty or unidentified entity fields in the scanned text.

The patient orchestration module 426 may access the patient data 416 and the prescriber data 418 to facilitate prediction of missing entity field values in the submitted document data 414. For example, if some patient entity fields in a document are missing values (such as a missing patient first name), the patient orchestration module may access the patient data 416 to predict the missing entity field value. In this example, if a patient last name and date of birth are both known based on the scanned document text, the patient orchestration module 426 may use the patient last name and date of birth to obtain a predicted first name value for the patient from the patient data 416. The system controller 408 can then fill in the missing value in the document before sending to the prescription fill processing module 410 for automated processing of the prescription fill request.

In various implementations, one or more modules of the system controller 408 may validate whether a predicted missing entity field value for the document is correct. For example, if a missing patient first name is obtained from the patient data 416 based on the known patient last name and date of birth, the system controller 408 may run the OCR module 422 on the document again (or analyze the output text from the original scan of the document by the OCR module 422), to confirm that the obtained patient first name is actually present in the document. This verification process for confirming that a predicted missing value is actually present in the document may reduce the occurrence of prescription fill errors.

As shown in FIG. 4, the system controller 408 may communicate with a prescription fill processing module 410 via the network(s) 104. For example, if an OCR rescan of the document indicates that the predicted missing entity field values are correct, the prescription fill may be processed automatically via the prescription fill processing module 410, using the predicted and verified values.

The document classification module 428 may classify a type of a document in order to determine which machine learning model should be used to perform entity recognition on the scanned text output for the document. For example, the document classification module 428 may access the document classification data 420 of the database 402 to determine whether a document belongs in a cover page category, a single page category, a multiple page prescription category, and so on.

Referring back to the database 402, the patient data 416 may include any suitable data records of patients and associated field values, such as a patient name, address, date of birth, phone number, and so on. The prescriber data 418 may include any suitable data records for prescribers and associated field values, such as a prescribing physician name, a prescriber address, a prescriber identifier (such as a drug enforcement administration registration number), a prescriber phone number, and so on. In various implementations, more or less (or other) data may be stored in the database 402. The database 402 may be considered as a record database where the patient data 416 includes multiple patient data structures and the prescriber data 418 includes multiple prescriber data structures.

Figure 5A:
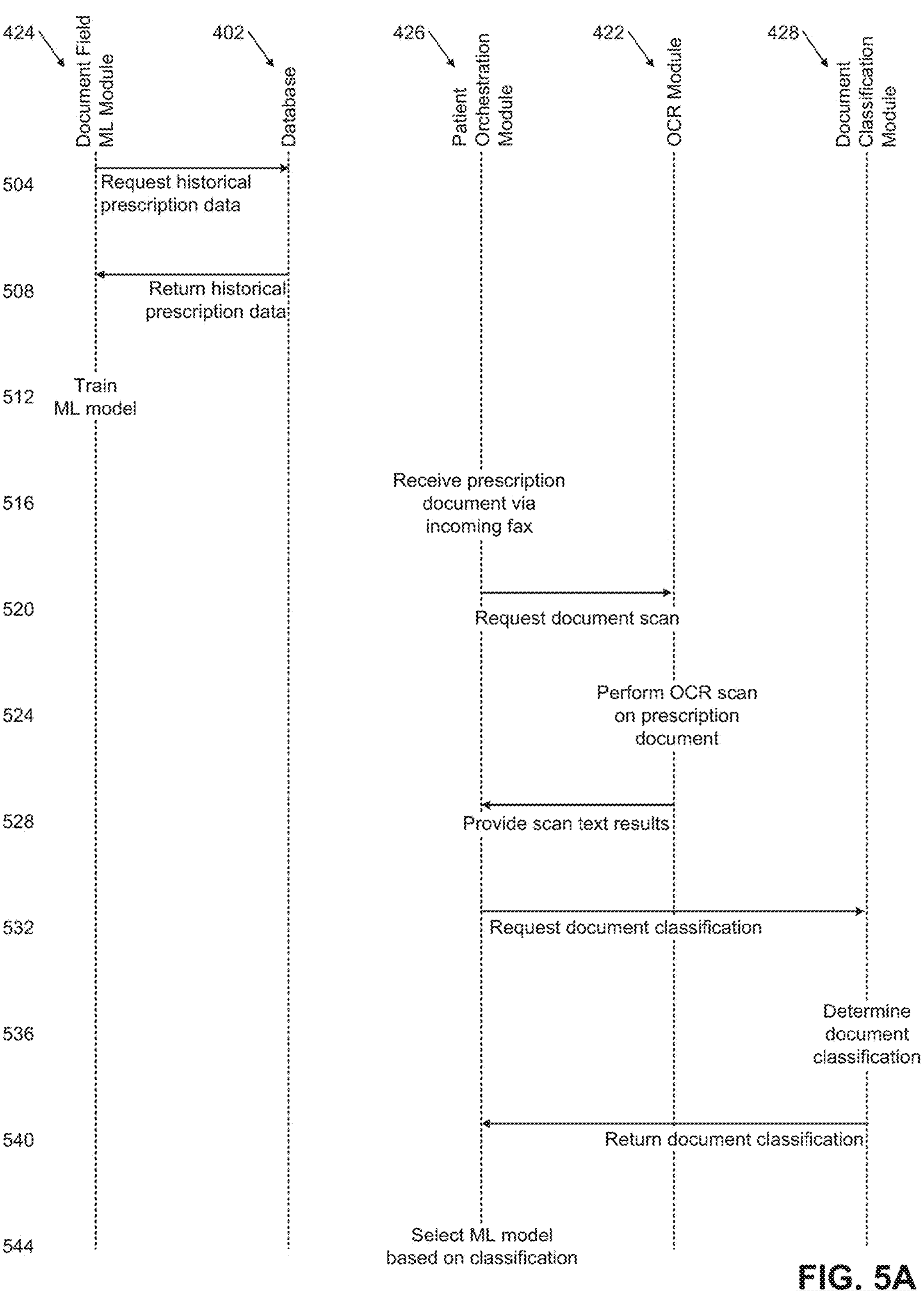
FIGS. 5A and 5B are message sequence charts illustrating example interactions between components of the system of FIG. 4.
Figure 5B:
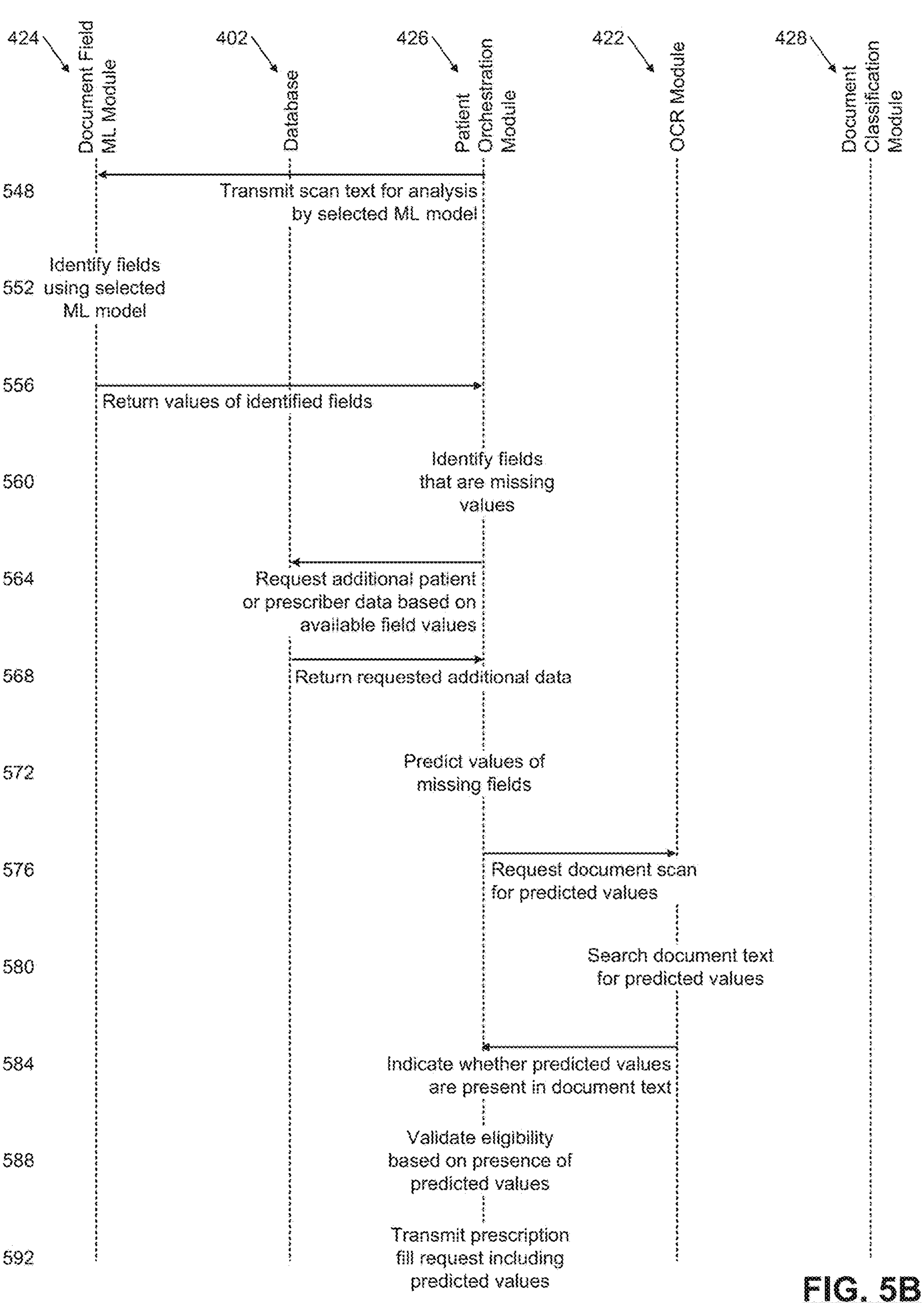

FIGS. 5A and 5B are message sequence charts illustrating example interactions between the database 402, the OCR module 422, the document field machine learning module

424, the patient orchestration module 426, and the document classification module 428. At line 504, the document field machine learning module 424 requests historical prescription data from the database 402.

For example, the historical prescription data may include the machine learning model data 412 or the submitted document data 414, for prescriptions that were previously requested and fulfilled via faxes received from a prescribing physician or other suitable prescription request method. At line 508, the database 402 returns historical prescription data to the document field machine learning module 424. The document field machine learning module 424 then trains the machine learning model at line 512.

At line 516, the patient orchestration module 426 receives the prescription document (sometimes referred to as an entity or database entity) via an incoming facsimile transmission. For example, a prescriber may transmit a request for a prescription fill that is stored in the submitted document data 414 of the database 402, or received directly by the system controller 408. Although FIG. 5A describes that the document is received via incoming fax, in various implementations the prescription request may be received via other suitable methods.

At line 520, the patient orchestration module 426 requests a document scan from the OCR module 422. The OCR module 422 then performs a document scan on the prescription fill request document at line 524. For example, the OCR module 422 may perform any suitable optical character recognition or other algorithm to automatically detect characters, words, phrases, other types of text, and so on, in the received prescription fill request document. The OCR module 422 then provides the text results of the scan back to the patient orchestration module 426, at line 528.

The patient orchestration module 426 requests a document classification from the document classification module 428, at line 532. The document classification module 428 then determines a classification type for the prescription fill request document at line 536. For example, the document classification module 428 may access the document classification data 420 from the database 402 in order to determine a classification type of the prescription fill request document, such as whether the prescription fill request document includes a cover page, whether the prescription fill request document is a single page prescription request or a multipage prescription request, and so on. The document classification module 428 then returns the identified document classification to the patient orchestration module 426 at line 540.

At line 544, the patient orchestration module 426 selects the machine learning module based on the received classification. For example, the document field machine learning module 424 may include multiple machine learning models that are used to process different types of documents. When the patient orchestration module 426 receives a document classification from the document classification module 428, the patient orchestration module 426 may identify a machine learning model that corresponds to the received document classification, such as a machine learning model that has been trained to process OCR data for prescription fill request documents that include a cover page.

As shown in FIG. 5B, at line 548 the patient orchestration module 426 transmits the scanned text output from the OCR module 422 to the document field machine learning module 424, for analysis by the selected machine learning model. The document field machine learning module 424 identifies fields in the scanned text output using the selected machine learning model, at line 552. For example, the scanned text output from the OCR module 422 may be input to the selected machine learning model to generate predicted entity fields and associated field values within the prescription fill request document. The document field machine learning module 424 then returns a value for each identified field to the patient orchestration module 426, at line 556.

At line 560, the patient orchestration module 426 identifies fields that are missing values. For example, when the patient orchestration module 426 receives the entity field values from the document field machine learning module 424, some of the identified fields may be empty or some expected fields may not have been detected at all in the document. As an example, if the patient orchestration module 426 receives a patient name entity field that has a blank value, or no patient name entity field is identified in the document, the patient orchestration module 426 may identify that the patient name entity field is missing or is missing a value.

The patient orchestration module 426 requests additional patient or prescriber data values from the database 402 (which may be based on known entity field values from the document), at line 564. For example, the patient orchestration module 426 may request the database 402 to provide patient data 416 or prescriber data 418 for entity fields that are identified as missing values. Examples of requesting specific missing entity field values are provided further below. The database 402 returns the requested additional data at line 568.

At line 572, the patient orchestration module 426 predicts values of the missing fields based on the data received from the database 402. For example, when the patient orchestration module 426 identifies a missing patient name field in the scanned document text, the patient orchestration module may predict, based on additional data received from the database 402, what the correct patient name value should be for the missing entity field value (such as an identified patient name from a record in the database that was accessed based on other known entity field values such as a patient date of birth and address in the prescription request document).

The patient orchestration module 426 requests a scan of the prescription fill request document from the OCR module 422 at line 576, to identify the predicted missing entity field values in the prescription request document. For example, after predicting a likely patient name to fill in the missing patient name entity field from the document, the patient orchestration module 426 may attempt to verify that the predicted patient name is correct by requesting the OCR module 422 to scan the document again in an attempt to locate the predicted patient name. The OCR module 422 then searches the document text for the predicted values at line 580, such as by using an optical character recognition process, which may be the same or different from the prior optical character recognition process performed by the OCR module 422 to originally identify text within the document. In various implementations, rescan of the document text may include analyzing the original scanned text output for the predicted missing entity field value, without performing a second optical character recognition process on the prescription fill request document.

At line 584, the OCR module 422 indicates to the patient orchestration module 426 whether the predicted values are present in the document text. For example, if the machine learning model was not able to identify a patient name field value in the original OCR scanned document text that was provided by the OCR module 422, but the patient orchestration module 426 was able to predict the likely patient name based on other available entity field values such as a patient date of birth and address, the OCR module 422 may rescan the document (or analyzed the original scan output text) to see if the predicted patient name is present in the prescription fill request document.

At line 588, the patient orchestration module 426 validates eligibility of the prescription fill request based on the presence or absence of the predicted values in the document text. For example, if the predicted patient name was found to be present in the document, the patient orchestration module 426 may determine that the predicted patient name for the missing patient name field is correct. If the predicted values for the missing entity fields are validated, the patient orchestration module 426 may transmit the prescription fill request including the predicted values, at line 592.

For example, the patient orchestration module 426 may transmit the prescription fill request to the prescription fill processing module 410 for automated processing of the prescription fill request (because the validation of the predicted patient name based on the rescan of the document text indicates a high confidence likelihood that the predicted patient name is correct). If the patient orchestration module 426 is unable to validate the missing field entity value, such as because the rescan of the document text did not detect the predicted patient name in the document, the patient orchestration module 426 may set aside the prescription fill request for manual review and approval by a system administrator.

As described above, in various implementations the system 400 may capture data from a received prescription request document, but sometimes is unable to identify all needed entity field values to automatically process the prescription fill. The system 400 may use information from, for example, an internal prescriber database or patient eligibility data, to identify missing or incorrect data fields in the received document. The system 400 may then rescan the document using OCR (or analyze originally scanned document text), to search for identified predicted values for the missing entity fields in the document.

In various implementations, the system 400 may use a machine learning model that is trained based on previous prescription request documents, to become more effective at identifying data elements on a fax document. Over time, the model may improve accuracy at identifying elements in the document during a first OCR scan of the document. Any predicted values for missing entity fields may be validated (such as by rescanning the document text to identify the presence of the predicted values), prior to populating the identified and predicted entity fields to an internal database for automated prescription fill processing.

Machine Learning Model

Figure 6:
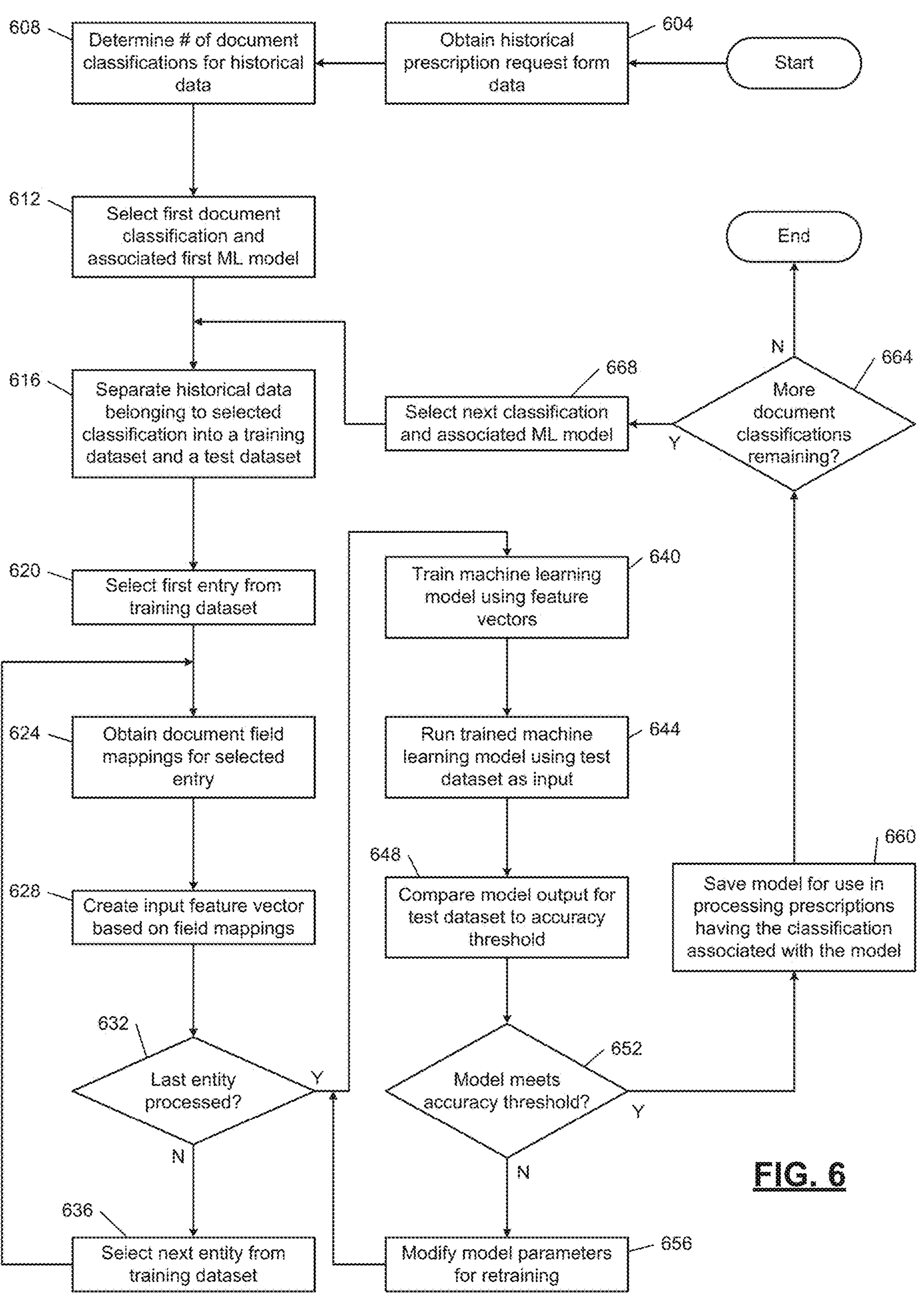
FIG. 6 is a flowchart depicting an example process for training a machine learning model to process prescription documents having entity fields.

FIG. 6 illustrates an example process for training a machine learning module, which may be performed by, for example, the document field machine learning module 424. Control begins at 604 by obtaining historical prescription request form data. For example, historical prescription request form data may be included in the machine learning model data 412 or the submitted document data 414 of the database 402.

At 608, control determines a number of document classifications for the historical data. For example, different prescription request documents may be classified into a certain number of categories, such as documents that include a cover page, documents have the prescription request details on a single page, documents that have prescription request details spanning multiple pages, and so on.

Control selects the first document classification and a machine learning model associated with the classification, at 612. Control then separates historical data belonging to the selected classification into a training dataset and a test dataset, at 616. For example, historical document data may be randomly divided where a portion of the data is used to train the model and another portion of the data is used to test the accuracy of the trained model.

At 620, control selects the first entry from the training dataset. Control then obtains document field mappings for the selected entry at 624. At 628, control creates an entity feature vector based on the field mappings. For example, because the historical document data may include prescription request forms that resulted in successful prescription fills, the correct field values associated with the document such as patient name, date of birth, address, and so on, may already be known based on the successful prescription fill associated with the document. In various implementations, an OCR process may be performed on each document to generate scanned text output for creating the input feature vectors. The scanned text output may be stored as structured scan data specific to a database entity (such as scanned text output of a prescription fill request document). Optionally, fuzzy matching may be performed on the OCR text output to create clean data elements for generation of the input feature vectors.

Control determines whether the last entity has been processed at 632. For example, if more document entities in the training dataset have not yet been processed to generate input feature vectors, control proceeds to 636 to select the next document from the training dataset and returns to 624 to obtain document field mappings for the next selected entry. Once control determines at 632 that all documents within the training set have been processed to create input feature vectors, control proceeds to 640 to train the machine learning model using the feature vectors. For example, control may supply the input feature vectors as inputs to the machine learning model associated with the selected document classification type. The machine learning model may generate an entity field output, where the entity field output includes multiple identified entity fields (such as a patient name and date of birth fields within a prescription fill request document), and values of the identified entity fields (such as the actual patient name and date of birth written or printed in the prescription fill request document).

At 644, control runs the trained machine learning model using the test dataset as the input (which may include creating input feature vectors for each document in the test dataset). Control then compares the model output for the test dataset to an accuracy threshold at 648. For example, any suitable threshold may be used that is indicative of a desired accuracy of entity field predictions by the machine learning model, such as at least 50% correct entity field determinations, at least 90% correct entity field determinations, and so on.

If control determines at 652 that the output of the trained model on the test dataset does not meet the specified accuracy threshold, control modifies the model parameters for retraining at 656, and then returns to 640 to retrain the machine learning model using the training dataset input feature vectors with the modified model parameters. For example, hyper parameters of the machine learning model may be tuned to increase the accuracy of the model output on the training dataset.

Once control determines at 652 that the model output meets a specified accuracy threshold, control proceeds to 660 to save the trained model for use in processing other prescription fill request documents that have a classification type associated with the model. For example, if a machine learning model has been trained based on prescription fill request documents having a cover page, the trained model may be stored to process future prescription requests that are classified as having a cover page document type.

Control then determines at 664 whether more document classifications are remaining. For example, if the number of document classifications is determined at 608 to include three document types, and machine learning models have been trained for the first two document types, control proceeds to 668 to select the next classification type associated with another machine learning model. Control then separates historical data belonging to that classification type into a training dataset and a test dataset at 616. Once control determines that there are no more document classifications types remaining for model training at 664, the process ends.

Figure 7A:
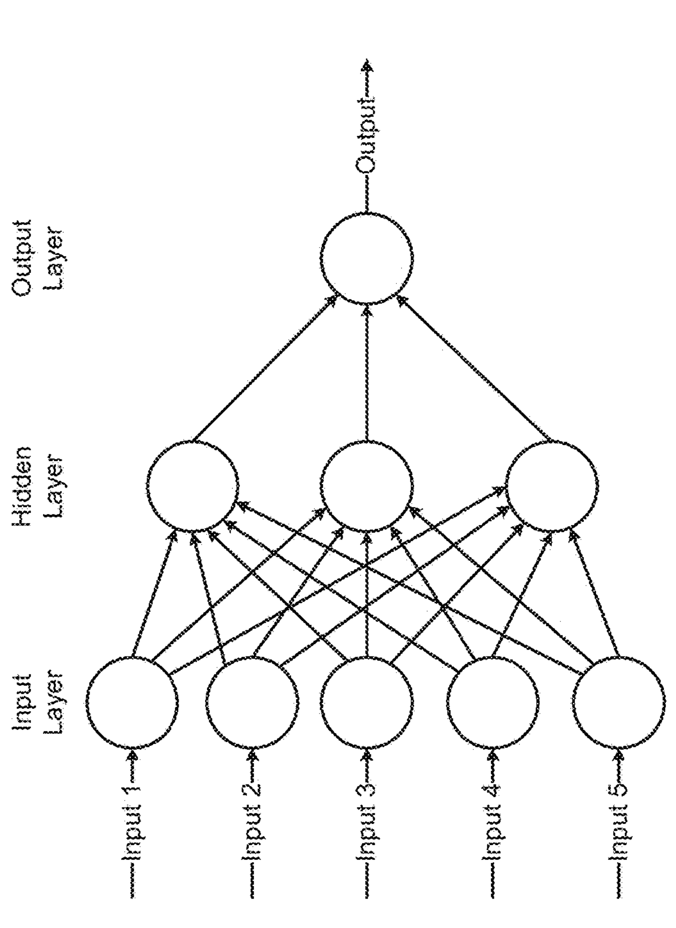
FIGS. 7A and 7B are graphical representations of example recurrent neural networks for generating machine learning models for automated entity field correction.
Figure 7B:
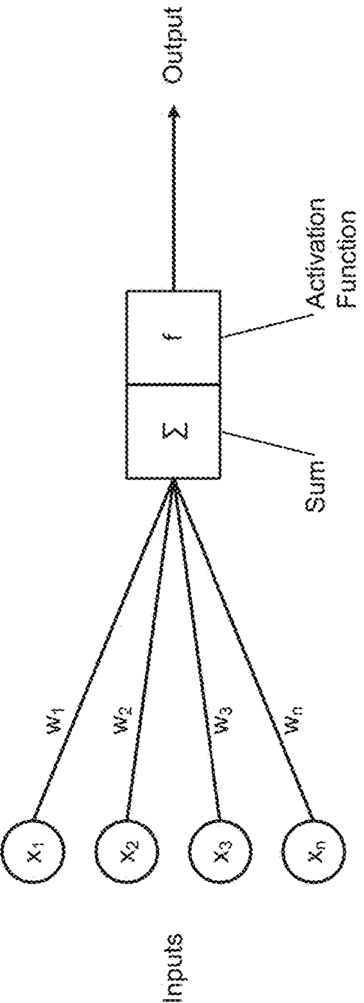

FIGS. 7A and 7B show an example of a recurrent neural network used to generate models such as those described above with reference to FIG. 6, using machine learning techniques. Machine learning is a method used to devise complex models and algorithms that lend themselves to prediction (for example, health plan customer predictions). The models generated using machine learning, such as those described above with reference to FIG. 6, can produce reliable, repeatable decisions and results, and uncover hidden insights through learning from historical relationships and trends in the data.

The purpose of using the recurrent neural-network-based model, and training the model using machine learning as described above with reference to FIG. 6, may be to directly predict dependent variables without casting relationships between the variables into mathematical form. The neural network model includes a large number of virtual neurons operating in parallel and arranged in layers. The first layer is the input layer and receives raw input data. Each successive layer modifies outputs from a preceding layer and sends them to a next layer. The last layer is the output layer and produces output of the system.

FIG. 7A shows a fully connected neural network, where each neuron in a given layer is connected to each neuron in a next layer. In the input layer, each input node is associated with a numerical value, which can be any real number. In each layer, each connection that departs from an input node has a weight associated with it, which can also be any real number (see FIG. 7B). In the input layer, the number of neurons equals number of features (columns) in a dataset. The output layer may have multiple continuous outputs.

The layers between the input and output layers are hidden layers. The number of hidden layers can be one or more (one hidden layer may be sufficient for most applications). A neural network with no hidden layers can represent linear separable functions or decisions. A neural network with one hidden layer can perform continuous mapping from one finite space to another. A neural network with two hidden layers can approximate any smooth mapping to any accuracy.

The number of neurons can be optimized. At the beginning of training, a network configuration is more likely to have excess nodes. Some of the nodes may be removed from the network during training that would not noticeably affect network performance. For example, nodes with weights approaching zero after training can be removed (this process is called pruning). The number of neurons can cause under-fitting (inability to adequately capture signals in dataset) or over-fitting (insufficient information to train all neurons; network performs well on training dataset but not on test dataset).

Various methods and criteria can be used to measure performance of a neural network model (such as for the model test result evaluation at 648 in FIG. 6). For example, root mean squared error (RMSE) measures the average distance between observed values and model predictions. Coefficient of Determination ($R^2$) measures correlation (not accuracy) between observed and predicted outcomes (for example, between trained model outputs and actual outputs of the historical testing data from the machine learning model data 412). This method may not be reliable if the data has a large variance. Other performance measures include irreducible noise, model bias, and model variance. A high model bias for a model indicates that the model is not able to capture true relationship between predictors and the outcome. Model variance may indicate whether a model is stable (a slight perturbation in the data will significantly change the model fit).

Figure 8:
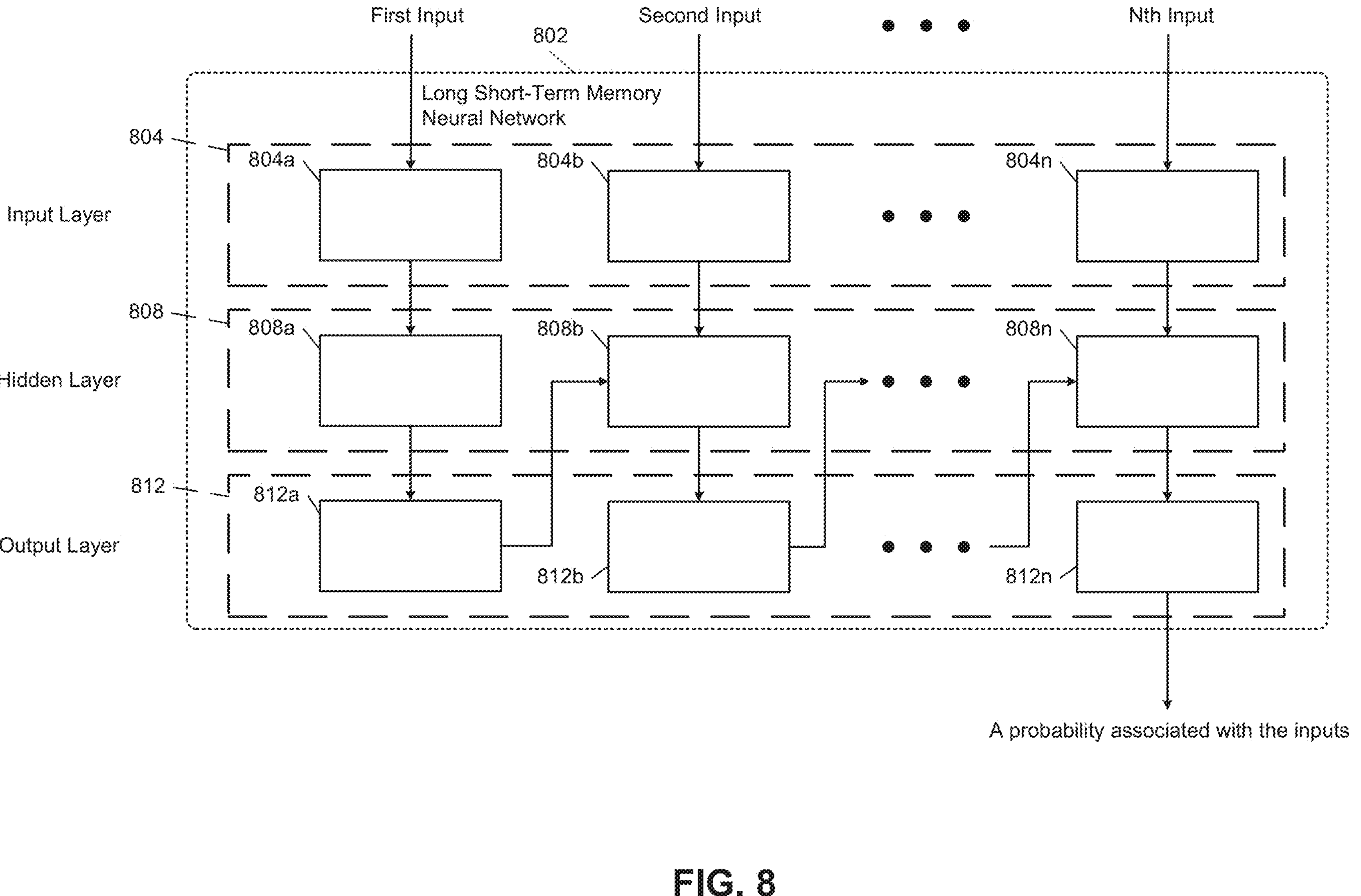
FIG. 8 is a graphical representation of layers or an example long short-term memory (LSTM) machine learning model.

FIG. 8 illustrates an example of a long short-term memory (LSTM) neural network used to generate models such as those described above with reference to FIG. 6, using machine learning techniques. Machine learning is a method used to devise complex models and algorithms that lend themselves to prediction (for example, predicting entity field values in scanned document text of a prescription fill request). The models generated using machine learning, such as those described above with reference to FIG. 6, can produce reliable, repeatable decisions and results, and uncover hidden insights through learning from historical relationships and trends in the data.

The purpose of using the recurrent neural-network-based model, and training the model using machine learning as described above with reference to FIG. 6, may be to directly predict dependent variables without casting relationships between the variables into mathematical form. The neural network model includes a large number of virtual neurons operating in parallel and arranged in layers. The first layer is the input layer and receives raw input data. Each successive layer modifies outputs from a preceding layer and sends them to a next layer. The last layer is the output layer and produces output of the system.

FIG. 8 is a functional block diagram of a generic example LSTM neural network 802. The generic example LSTM neural network 802 may be used to implement the machine learning model trained by the process of FIG. 6, and various implementations may use other types of machine learning networks. The LSTM neural network 802 includes an input layer 804, a hidden layer 808, and an output layer 812. The input layer 804 includes inputs 804*a*, 804*b* . . . 804*n*. The hidden layer 808 includes neurons 808*a*, 808*b* . . . 808*n*. The output layer 812 includes outputs 812*a*, 812*b* . . . 812*n*.

Each neuron of the hidden layer 808 receives an input from the input layer 804 and outputs a value to the corresponding output in the output layer 812. For example, the neuron 808*a* receives an input from the input 804*a* and outputs a value to the output 812*a*. Each neuron, other than the neuron 808*a*, also receives an output of a previous neuron as an input. For example, the neuron 808*b* receives inputs from the input 804*b* and the output 812*a*. In this way the output of each neuron is fed forward to the next neuron in the hidden layer 808. The last output 812*n* in the output layer 812 outputs a probability associated with the inputs 804*a*-804*n*. Although the input layer 804, the hidden layer 808, and the output layer 812 are depicted as each including three elements, each layer may contain any number of elements.

In various implementations, each layer of the LSTM neural network 802 must include the same number of elements as each of the other layers of the LSTM neural network 802. For example, historical patient data may be processed to create the inputs 804*a*-804*n*. The output of the LSTM neural network 802 may represent likely entity field values within a prescription fill request document.

In some embodiments, a convolutional neural network may be implemented. Similar to LSTM neural networks, convolutional neural networks include an input layer, a hidden layer, and an output layer. However, in a convolutional neural network, the output layer includes one fewer output than the number of neurons in the hidden layer and each neuron is connected to each output. Additionally, each input in the input layer is connected to each neuron in the hidden layer. In other words, input 804*a* is connected to each of neurons 808*a*, 808*b* . . . 808*n*.

In various implementations, each input node in the input layer may be associated with a numerical value, which can be any real number. In each layer, each connection that departs from an input node has a weight associated with it, which can also be any real number. In the input layer, the number of neurons equals number of features (columns) in a dataset. The output layer may have multiple continuous outputs.

As mentioned above, the layers between the input and output layers are hidden layers. The number of hidden layers can be one or more (one hidden layer may be sufficient for many applications). A neural network with no hidden layers can represent linear separable functions or decisions. A neural network with one hidden layer can perform continuous mapping from one finite space to another. A neural network with two hidden layers can approximate any smooth mapping to any accuracy.

Entity Field Validation

Figure 9:
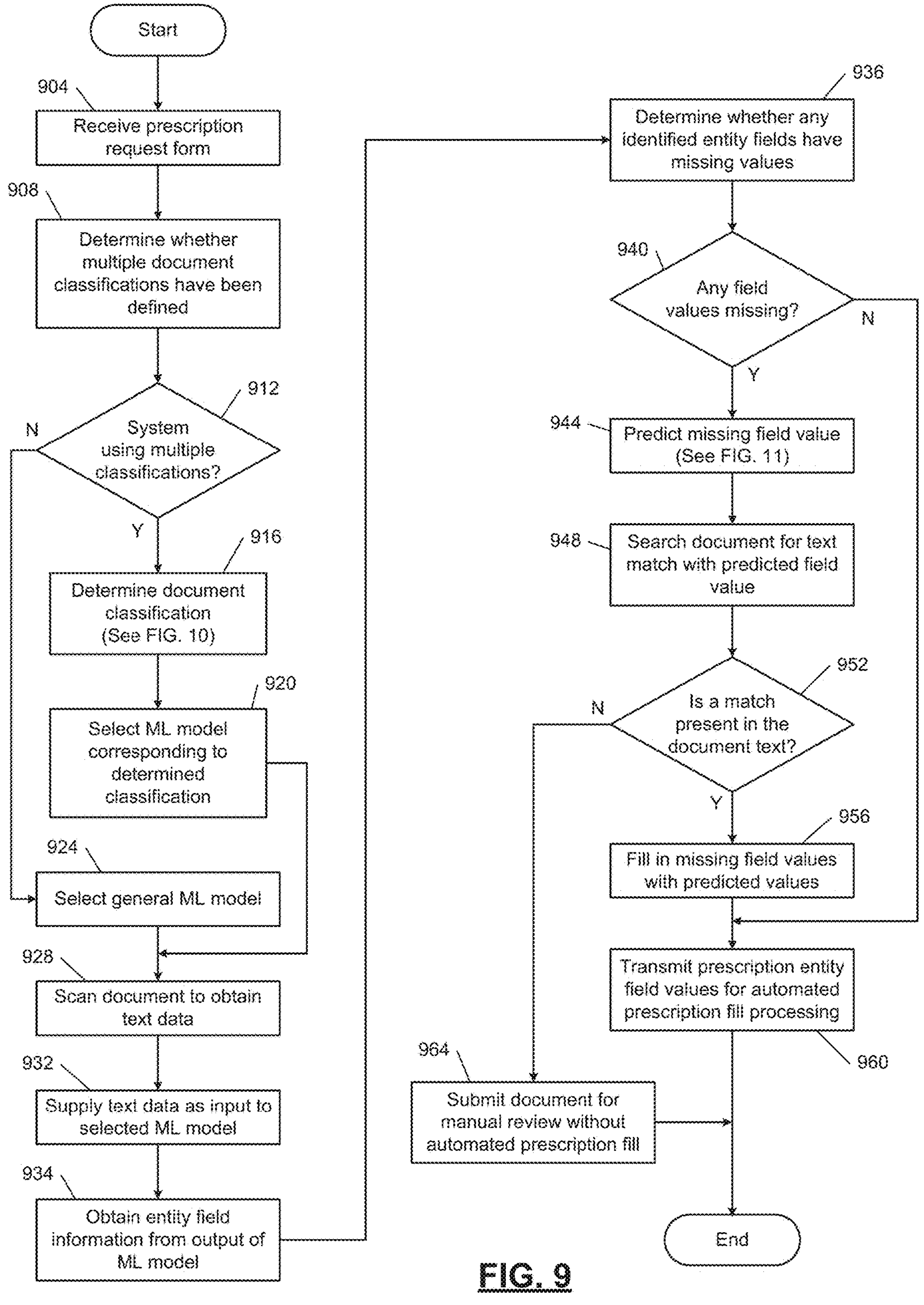
FIG. 9 is a flowchart depicting an example process for validating entity fields of a prescription document.

FIG. 9 illustrates an example process for validating predicted values of missing entity fields in a document. In various implementations, the process of FIG. 9 may be performed by one or more of the OCR module 422, the document field machine learning module 424, the patient orchestration module 426, and the document classification module 428 of FIG. 4.

At 904, control begins by receiving the prescription fill request form. The prescription fill request form may be received directly from a prescriber, such as via fax, or by accessing the submitted document data 414 in the database 402. At 908, control determines whether multiple document classifications have been defined for analysis of the prescription fill request. For example, in various implementations documents may be classified into one of multiple types, such as a document having a cover page, a document having prescription fill details on a single page, a document having prescription fill details on multiple pages, and so on.

If control determines at 912 that the system does not include multiple classifications, control proceeds to 924 to select a general machine learning model, and scans the document to obtain scanned text data at 928. If control determines at 912 that the system does include multiple document classifications, control determines a classification type for the received document at 916. An example for determining a document classification is described further below with reference to FIG. 10. After identifying a document classification type for the received document, control proceeds to 920 to select a machine learning model corresponding to the identified classification type, and then scans the document to obtain text data at 928.

After scanning the document to obtain the text data at 928, which may be performed by the optical character recognition module 422, control supplies the scanned text output as input to the selected machine learning model at 932. For example, the selected machine learning model may be a general machine learning model if system has not been set up to use multiple document classification, or the selected machine learning model may correspond to a determined classification type of the prescription fill request document.

At 934, control obtains identified entity fields and associated values from the output of the machine learning model. For example, the machine learning model processes the OCR output text of the scanned document to identify entity fields and their associated values within the scanned output text. Control then determines at 936 whether any identified entity fields have missing values, or whether an expected entity field such as the patient name of the date of birth is not detected in the document text.

If control determines at 940 that no entity field values are missing, control proceeds to 960 to transmit the prescription data including the identified field values for automated prescription fill processing. For example, if control determines that there are no entity fields missing that are missing values, control may transfer the prescription fill request to the prescription fill processing module 410 for automated prescription fill processing.

If an expected entity field of the document is missing a value or the expected entity field was not identified within the scanned document text, control proceeds to 944 to predict the value of the missing entity field. An example process for predicting missing field values is described further below with reference to FIG. 11. Once the predicted missing field values are obtained, control proceeds to 948 to search the document text in an attempt to identify the presence of the predicted field values. For example, the OCR module 422 may rescan the document to look for the predicted field values in the document text, or the original scanned output text may be searched to locate the predicted field values.

If control determines at 952 that a match is present in the document text for the predicted missing entity field value, control proceeds to 956 to fill in the missing field values with the predicted values. Control then transmits the prescription entity field values for automated prescription fill processing. For example, if control predicts a missing patient first name based on a patient last name and date of birth record in the database 402, and the OCR module 422 is able to scan the document to locate the predicted patient first name obtained from the record, control may determine that the predicted patient first name is likely correct. Control may then fill in the missing patient first name field within the document data before transmitting the prescription fill request for automated processing at 960.

In various implementations, when control validates a predicted missing entity field value by identifying a match for the predicted value in the scanned document text, control may assign the entity to a validated subset of the prescription fill request documents. The documents within the subset may then be sent to the automated fill processing module at 960.

If control determines at 952 that the predicted field value does not have a match within the document text, control proceeds to 964 to submit the document for a manual review by a system administrator or prescription fill technician. In this case, control may not automate a fill of the prescription request because the system was unable to confirm all required field values within the document to ensure correct automated processing.

Figure 10:
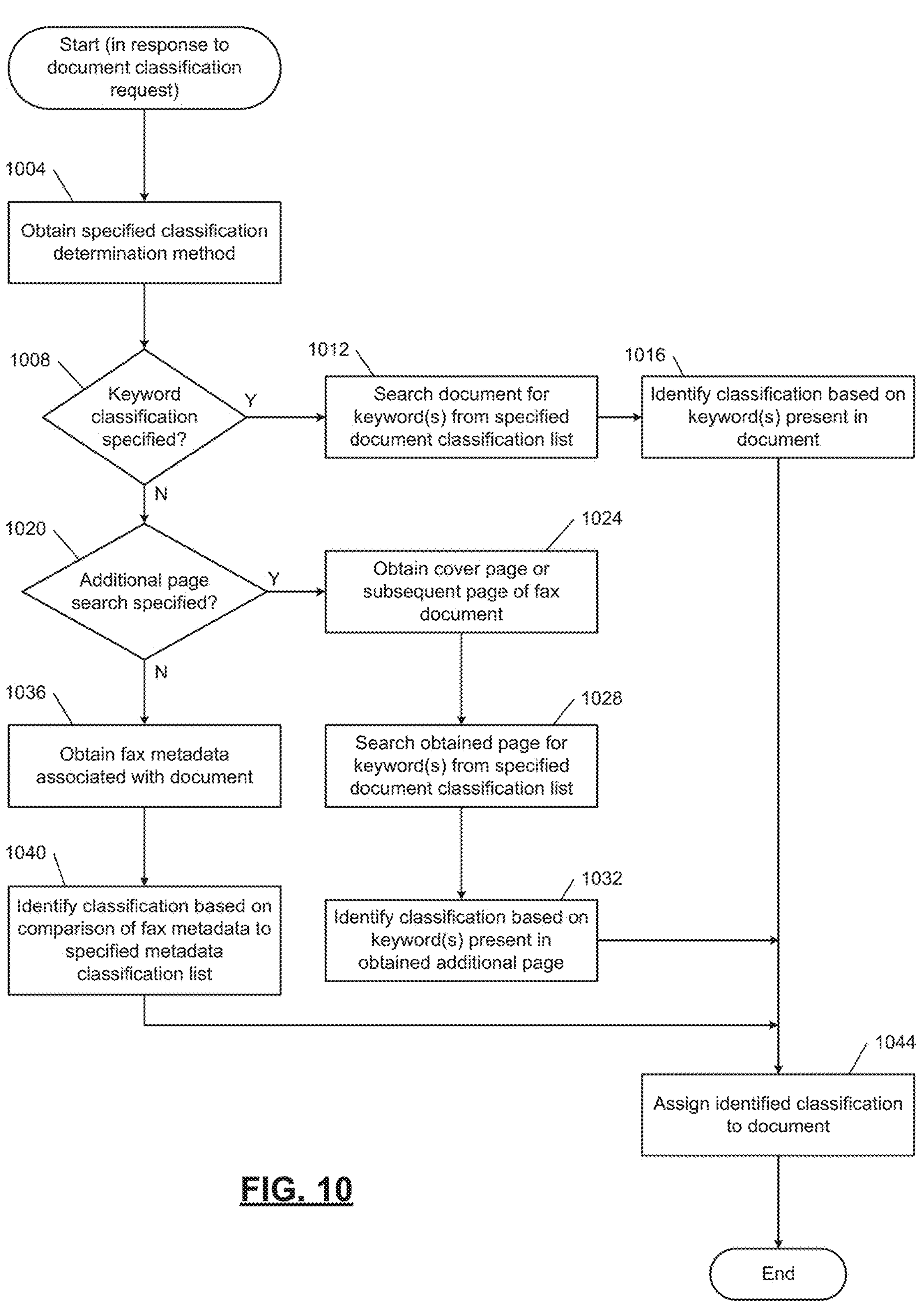
FIG. 10 is a flowchart depicting an example process for classifying a prescription document having entity fields.

FIG. 10 illustrates an example process for determining a classification of a received prescription fill request document (such as a document received from a prescriber via fax). The process of FIG. 10 may be performed by, for example, the document classification module 428 of FIG. 4. In response to a document classification request, control obtains a specified classification determination method at 1004. For example, documents may be classified according to one or more classification methods, such as keyword classification, page number classification determination, fax metadata analysis, and so on.

At 1008, control determines whether keyword classification has been specified. In various implantations, the document classification determination method may be specified by a system administrator, or set up in application settings of the document classification module 428. If control determines at 1008 that the keyword classification method has been specified, control proceeds to 1012 to search the document for keywords from a specified document classification list. For example, each document classification type may have an associated list of keywords that, when present within the prescription fill request document, indicate the document likely belongs to that classification type. At 1016, control identifies a classification type based on keywords present in the document, and assigns the identified classification to the document at 1044.

If control determines at 1008 that keyword classification has not been specified, control proceeds to 1020 to determine whether additional page searching has been specified. If so, control proceeds to 1024 to determine whether the document includes a cover page or one or more subsequent pages, and obtains the page(s) if present. For example, some prescription fill request documents may or may not include a cover page, and may or may not include multiple pages of prescription fill details. Control may analyze the document to determine the number of pages present, whether one of the pages is a cover page, and so on, in order to determine how to classify type of document.

In various implementations, control may search an obtained first page, subsequent page, or cover page, for keywords associated with a specified document classification, at 1028. For example, depending on whether multiple pages are used, whether a cover page is used, and so on, control may search relevant pages to identify keywords that determine a type of classification for the prescription fill request document. Control then identifies a classification at 1032 based on the keywords present in the numbered pages, and assigns the identified classification to the document at 1044.

In various implementations, control may use sequence rules that are executed against configurable label datasets that includes lists on inclusion and exclusion for specified entities. Control may lookup patterns to identify a Note or Cover page in a scanned image, to identify a PRIOR_AUTH classification in a scanned image, to identify a vendor specific EMR classification in a scanned image, to identify a HAQ form in a scanned image, to determine whether a document has a barcode, or any other suitable classification techniques based on keywords. Control may classify a document based on contents of a cover letter of a fax.

If control determines at 1020 that a page number classification method has not been specified, control obtains fax metadata associated with the document at 1036. For example, in various implementations metadata associated with the fax document may be used to determine a classification type of the document. Control proceeds to 1040 to identify a classification based on the fax metadata of the document. In various implementations, different types of fax metadata may be associated with different document classifications, and a mapping of the fax metadata may be stored in a list for classification of received documents. Control then assigns the identified classification to the document at 1044.

In various implementations, control may classify a document based on a vendor source in the fax metadata, such as a sure script vendor. The documents may be classified based on a source ANI, or a combination of configurable datasets for the fax source information.

Text may classification may include converting words into numerical values via word encoding or tokenization. For example, a token dictionary may include all unique words in a source of text (e.g., a vocabulary), where a different integer value is assigned to each word in the vocabulary. In this example, a sample text may be converted to a tokenized text by replacing each word in the text with its corresponding token according to the token dictionary, to create a tokenized vector of the text.

In order to create a more dense representation, a learned word vector sometimes referred to as an embedding may be used. Word embeddings may include vectors of a specified length, such as a vector of 100 (or more or less) values. Each vector may represent a single word, where the values in each column represent features of a word, rather than any specific word. For example, in a word2vec embedding, the word "the" may have a vector of [0.2, 0.4, −0.1], the word "good" may have a vector of [0.7, −0.5, 0.3], and the word "movie" may have a vector of [0.1, 0.2, 0.6]. Although three column values are listed for each word, various implementations may include vectors of 100 columns, 300 columns, etc., for each word.

In various implementations, a convolutional kernel may be used to look at embeddings for multiple words via a sliding window. A convolutional neural network may include many of these kernels, and as the network trains, kernel weights are learned. Each kernel may be designed to look at a word, and surrounding word(s) in a sequential window, and output a value that captures something about the phrase. In this manner, the convolution operation may be viewed as window-based feature extraction, where the features are patterns in sequential word groupings that indicate traits like sentiment of a text, grammatical function of different words, and so on. Using the above example, a convolutional kernel of [0.5, 0.4, 0.7; 0.2, −0.1, 0.3] could be applied to the words "good" and "movie" to generate a convolutional kernel output of 0.54.

In order to process an entire sequence of words, a convolutional kernel may slide down a list of word embeddings, in sequence. This may be referred to as a one-dimensional (1D) convolution because the kernel is moving in a single dimension: time. The output of the 1D convolution may be a feature vector with one convolution output value for each point in time of the sliding convolution kernel. For example, if the convolutional kernel has a height of three words, the first value in the output feature vector may be a result of applying the convolutional kernel to the first three words in the list of word embeddings, the second value in the output feature vector may be a result of applying the convolutional kernel to the second through fourth words in the list of word embeddings, and so on.

In various implementations, multiple filters of different heights may be used to learn a variety of different relationships between words. In one example, 300 kernels total may be used, with 100 kernels at a height of 3, 100 kernels at a height of 4, and 100 kernels at a height of 5. In other implementations, more or less kernels may be used, at greater or lesser heights. As the convolutional kernel slides over word embeddings one at a time, it captures local features or features within a nearby window of sequential words. The stacked output feature vectors that arise from multiple convolutional operations may be referred to as a convolutional layer.

A feature vector may be used to look for an important phrase in a text source, such as "great plot" when classifying movie reviews as positive or negative. In this example, the location of the phrase may not be important, just the fact that the phrase is present in the text (e.g., because "great plot" used anywhere in the text may suggest the text is a positive review). In order to indicate the presence of a high-level feature, it may be identified in the vector regardless of its location within a larger input sequence. In some example embodiments, this may be implemented by discarding less relevant locational information, using a maxpooling operation. The maxpooling operation may force a network to retain only the maximum value in a feature vector, which may be the most useful local feature. For example, if the maximum value in a feature vector output is 0.8, the maxpooling operation applied to the feature vector may result in an output of only the value 0.8. Because the maxpooling operation often looks at a sequence of local feature values, it may be referred to as maxpooling over time.

In various implementations, a multilayer perceptron network may be used, which is a class of feedforward artificial neural networks. The term MLP may be used to loosely refer to any feedforward ANN, or to strictly refer to networks including multiple layers of perceptrons. In some example embodiments, maximum values produced by processing each convolutional features vector may be concatenated and passed to a final, fully-connected layer, which may produce as many class scores as a text classification task requires.

A complete network may receive a batch of texts as input. The input may go through a pre-trained embedding layer, followed by the sequences of word embeddings going through multiple convolutional operations with kernel heights of three, four and five (or any other suitable heights). These layers may then go through a ReLu activation and maxpooling operation. Finally, the max-values from the three different convolutional layers may be concatenated and passed to a final, fully-connected classification layer. In various implementations, document classification may be performed using one or more of the above approaches (or other suitable document classification techniques) in order to classify documents for processing by the system 400.

Figure 11:
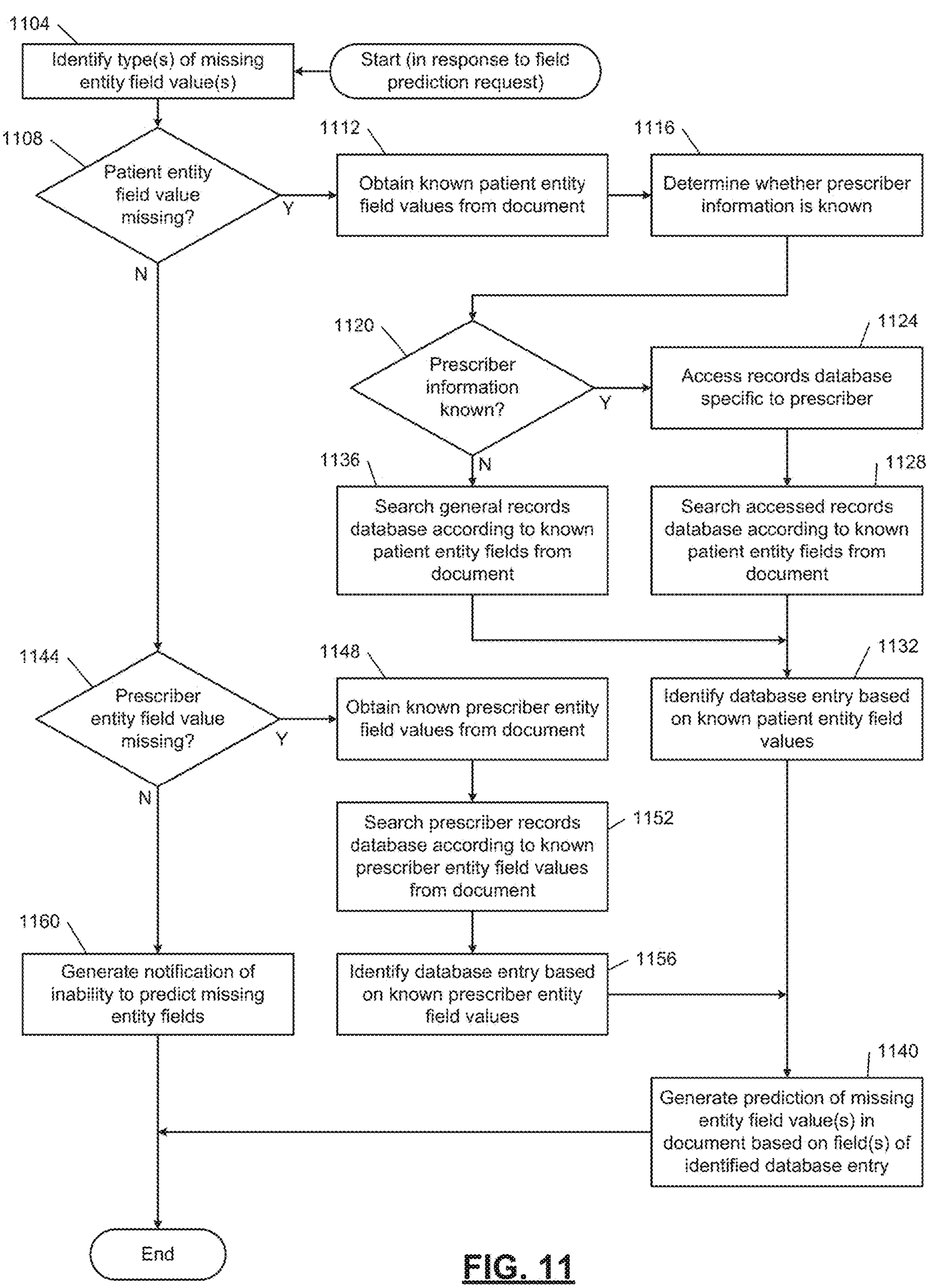
FIG. 11 is a flowchart depicting an example process for predicting missing entity fields in a prescription document.

FIG. 11 illustrates an example process for predicting values of missing entity fields, such as missing entity fields in scanned text of a received prescription fill request document. At 1104, control identifies types of missing data field values. For example, different entity fields may have information related to patients, related to prescribers, or other categories of prescription request data.

At 1108, control determines whether patient entity field values are missing. If so, control proceeds to 1112 to obtain other known patient entity field values from the document. For example, if the patient first name is missing, control may obtain a patient last name field value, patient date of birth field value, a patient address field value, and so on, from the scanned document text.

At 1116, control determines whether prescriber information is known (for example, if the scanned document text includes known prescriber entity field values). If control determines at 1120 that prescriber information is known, control proceeds to 1124 to access records in a database that are specific to the identified prescriber. For example, control may access the prescriber data 418 in the database 402 of FIG. 4.

Control then searches the accessed record(s) in the database according to known patient entity field values from the scanned document text, at 1128. For example, if a specific prescriber of the prescription fill request is known based on prescriber entity field values in the document (or other prescriber information obtained by the system), control may search a database specific to the identified prescriber in order to identify missing patient entity field values.

If control determines at 1120 that the prescriber information is not known, control proceeds to 1136 to search a general database for records according to known patient entity fields from the document. For example, control may access the patient data 416 of the database 402 in order to fill missing patient entity fields. In various implementations, control may identify one or more records based on known patient entity field values, such as by looking up a record entry based on a street address and date of birth that were identified for the patient from the scanned document text. Control may then use the identified record entry to predict missing patient field entity values from information associated with the identified patient record.

At 1132, control identifies a database record entry based on known patient entity field values, and then generates a prediction of the missing data field values at 1140, based on the identified record entry. As an example, if known patient entity fields in the scanned document text specify a last name and date of birth for a patient, control may identify a patient record having the same last name and date of birth in a record database, and then predict that the first name of the stored patient record is likely the missing patient name value for the prescription fill request document. Control may search the record database (such as the database 402) for a predicted value that has been stored in association with at least one known entity field value in, for example, a patient data structure or prescriber data structure.

In various implementations, any suitable combination of known data fields may be used to identify or predict missing entity field values. For example, control may use known prescriber information to search a prescriber-patient history database by National Provider Identifier (NPI) for patient last name, first name or date of birth (DOB) matches, or may search a patient Rx history by patient last name, first name or DOB, to match other missing entity field values or last name, first name or DOB. A lookup may be performed based on an address, DOB, phone number or patient name as identified by a machine learning model, to match missing entity field values of a patient name or DOB. A patient data application programming interface (API) may be used to predict missing patient entity fields, missing city/state and zip code information may be searched via patient records, and so on. Control may filter patient data records according to known prescriber information when possible, to reduce the search results for identifying missing patient entity fields.

If control determines at 1108 that no patient entity field values are missing, control proceeds to 1144 to determine whether any prescriber entity field values are missing. If so, control obtains known prescriber entity field values from the document at 1148. Control then searches for prescriber records in a database according to the known prescriber entity field values in the scanned document text, at 1152.

In various implementations, control may access the prescriber data 418 of the database 402, to identify prescriber records based on known prescriber entity field values from the document. For example, if a prescriber name and identifier number have been identified in scanned document text, control may look up a prescriber record based on the name and identifier number in order to predict a missing prescriber address field that was not identified by an original OCR scan of the prescription fill request document. At 1156, control identifies a database entry record based on the known prescriber entity field values, and then generates a prediction of the missing prescriber entity field values in the document based on the identified prescriber record entry, at 1140.

If prescriber information is missing, control may use known patient entity fields to search a patient-prescriber history by member number to lookup prescriber details. Control may search a prescriber dictionary using an NPI or DEA number of the prescriber, a name or phone number, a city or state, a phone number or address read by a machine learning model, and so on.

If control determines at 1144 that no prescriber entity field values are missing, control may proceed to 1160 to generate a notification of an inability to predict missing entity field values in the document. For example, if control is unable to identify a type of missing field value, or the missing entity field value is not of a type in which control may access records to make a prediction for the missing entity field, control may generate a notification that is not able to predict the missing entity field value. Although patient and prescriber entity field values are illustrated in FIG. 11, various implementations may use other suitable types of entity fields for prediction of missing field values. Once all requested missing entity field values have been predicted using the process of FIG. 11, the process ends.

FIG. 12 illustrates an example of the entity field recognition for scanned text output of a prescription fill request document. The scanned text output 1202 illustrated on the left side of FIG. 12 may be text output from, for example, the OCR module 422 of FIG. 4. In various implementations, the scanned text output 1202 may be a result of performing optical character recognition on a prescription fill request document.

The entity field document 1204 illustrated on the right side of FIG. 12 may be a result of performing entity field recognition on the scanned text output 1202. For example, the document field machine learning module 424 of FIG. 4 may supply the scanned text output 1202 as input to a trained machine learning model to generate the entity field document 1204.

As shown in FIG. 12, the entity field document 1204 has double underlined entity fields that have been identified by the machine learning model, as well as the associated field values. For example, "John Smith" is identified as the patient name entity field, "123 Clinton Avenue" is identified as a patient address entity field, and "83232" is identified as a patient zip code entity field. Similarly, "Osheroff, Joseph, MD" is identified as a prescriber name entity field, "B04507779" is identified as the prescriber DEA identifier entity field, and "10630 Little Patuxent" is identified as the prescriber address entity field. The entity fields are highlighted for purposes of illustration only, and various implementations may include other suitable fields.

Fuzzy Match Algorithms

Figure 13:
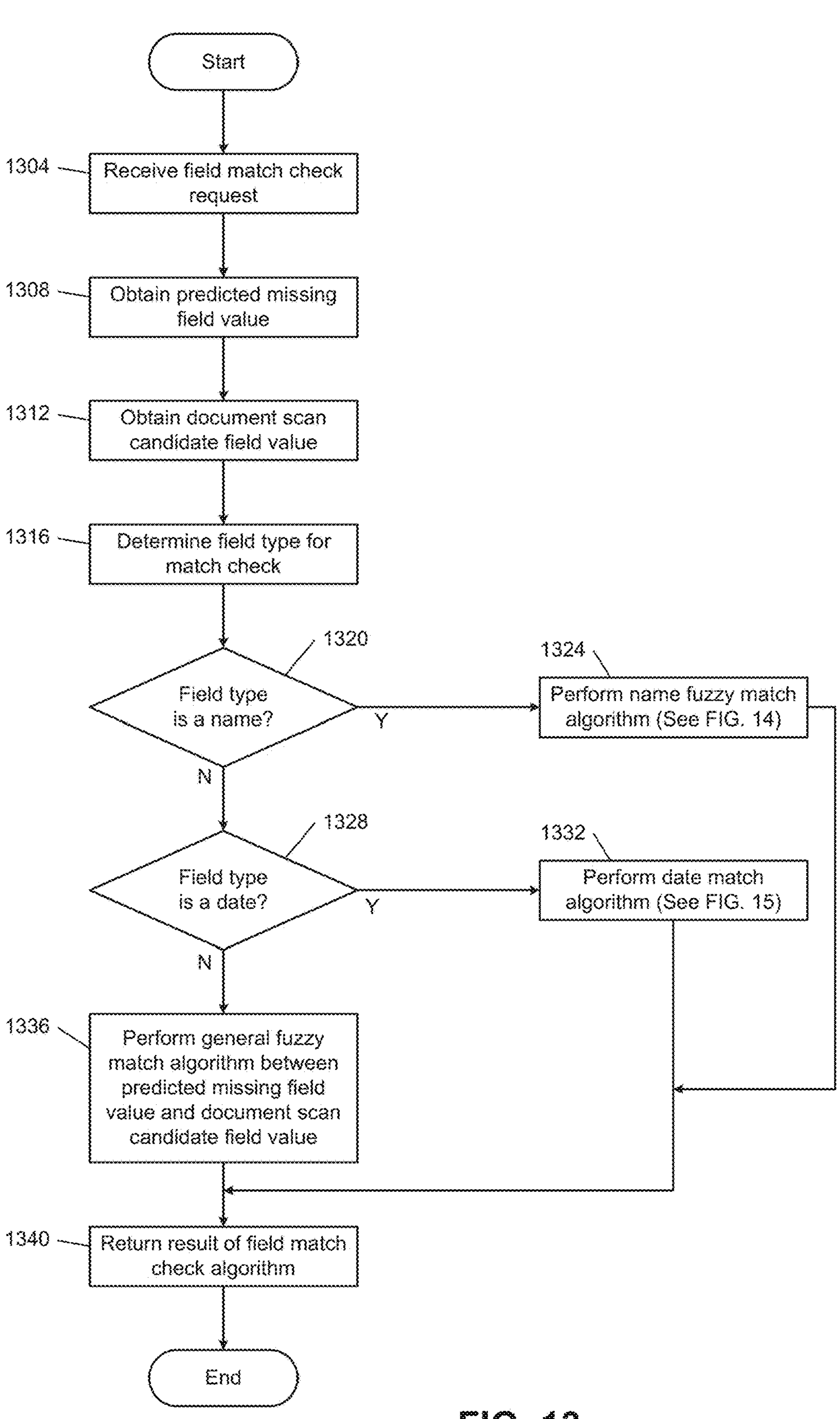
FIG. 13 is a flowchart depicting an example process for determining whether a document scan field matches a predicted missing field value.
Figure 14:
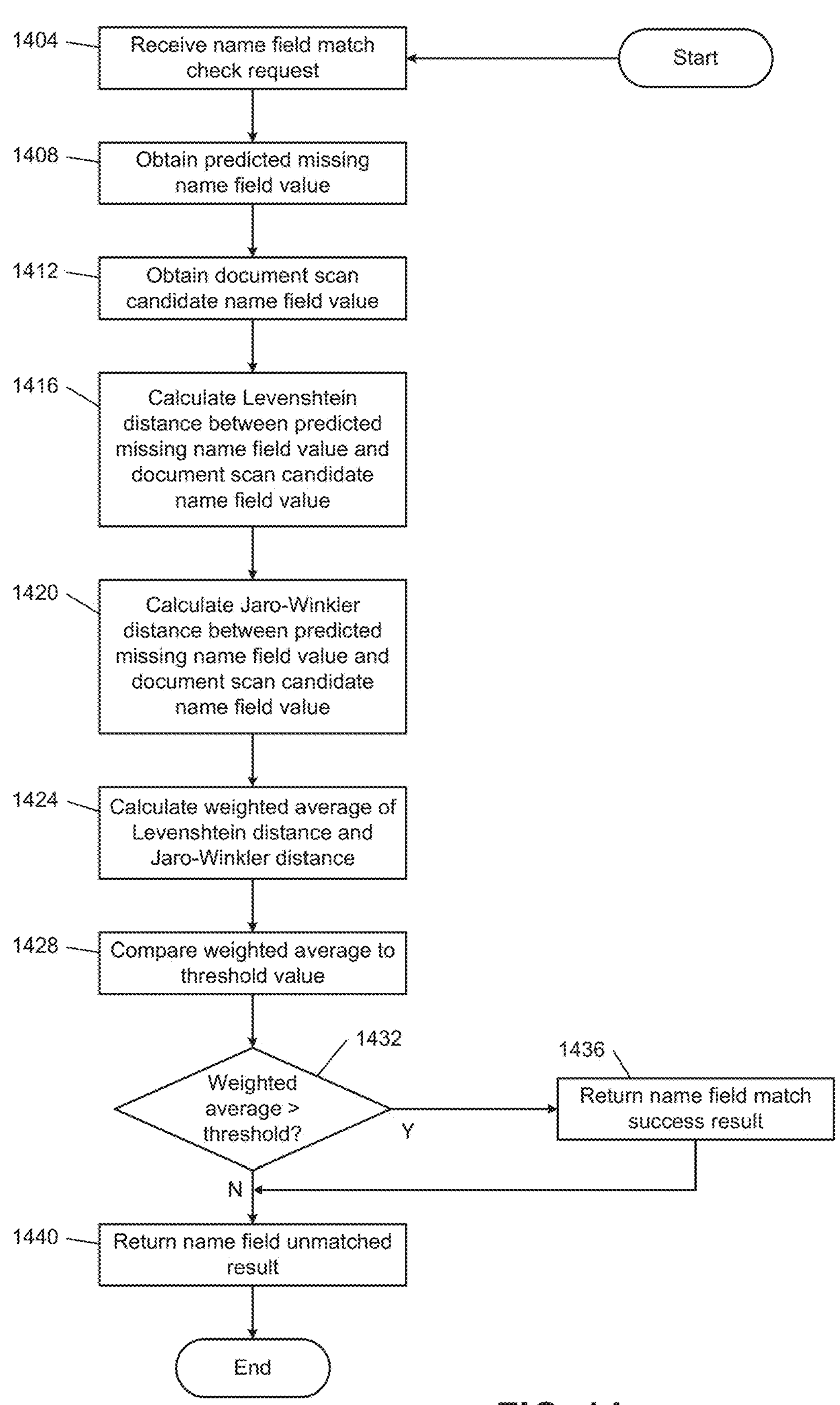
FIG. 14 is a flowchart depicting an example process for determining whether a document scan name field matches a predicted missing name field value.
Figure 15:
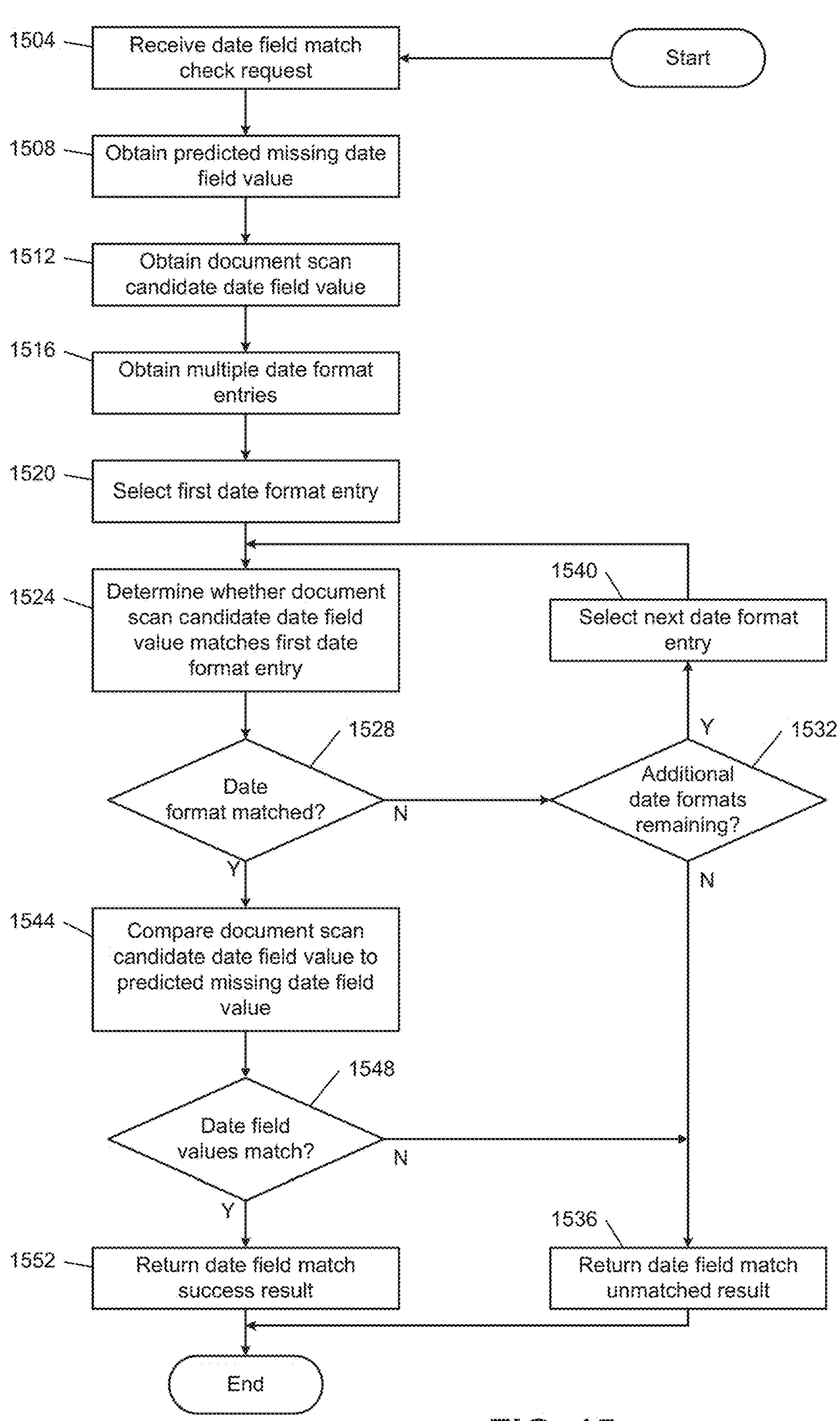
FIG. 15 is a flowchart depicting an example process for determining whether a document scan date field matches a predicted missing date field value.

FIGS. 13-15 illustrate examples of fuzzy matching using various algorithms to improve validation of predicted values in scanned documents, and reduce or avoid incorrect fuzzy matching. For example, fuzzy matching may be used to determine whether a predicted value match is present in the document, such as at step 952 in the example algorithm illustrated in FIG. 9, as described above.

In particular, FIG. 13 is a flowchart depicting an example process for determining whether a document scan field matches a predicted missing field value. Control begins at 1304 by receiving a field match check request. For example, after obtaining a predicted missing field value, control may request a fuzzy match algorithm (or other suitable matching algorithm) to determine whether the predicted missing field value is present in the scanned document (such as by analyzing previously stored scanned document data, or by rescanning the document).

At 1308, control obtains the predicted missing field value (for example, from an output of the example method for predicting a missing field value illustrated in FIG. 11). In various implementations, the predicted missing field value may be obtained by using known field entries to lookup an expected or predicted value for a missing field. Table 1 below illustrate various examples of missing patient fields, prescriber fields, etc., that may be looked up based on other known fields values obtained from the scanned document.

TABLE 1

| |
|---|
| Patient Predict Using Prescriber Information verified look into Prescriber-Patient History by NPI and match by Last Name, First Name and DOB |
| Patient Predict Lookup Patient Rx History by Last Name and First Name and match by Last Name, First Name and DOB |
| Patient Predict Lookup Patient Rx History by Last Name or First Name and DOB and match by Last Name, First Name and DOB |
| Patient Predict Lookup by Machine Learning read Address or by Last Name, or First Name, Phone or DOB and match by Last Name, First Name and DOB |
| Patient Predict Lookup by Machine Learning read DOB and Last Name or First Name and Phone and match by Last Name, First Name and DOB |
| Patient Predict Lookup by Machine Learning read DOB and Last Name or First Name and Phone and match by Last Name, First Name and DOB |
| Patient Predict Success by ML data Only |
| Patient Predict Success by reverse lookup using Phone |
| Patient Predict Success by reverse lookup using Address |
| Prescriber Predictive Phone Match Override Failure |
| Prescriber Predictive Analytics Success |
| Patient Predictive Analytics Success using Person API |
| Predict Zip by City and State |
| Predict Zip and State by City |
| Predict City and State by Zip |
| Predict Default 00 Century to 20 |
| Predict Default 00 Century to 19 |
| Predict First Name using PredictElements by Last Name |
| Predict Last Name using PredictElements by First Name |
| Predict DOB using PredictElements |
| Patient Verified using Exact DOB match and Exact or Fuzzy Name match |
| Patient Predict Elements Lookup Patient Rx History by Last Name and First Name and match by Last Name, First Name and DOB |
| Patient Predict Elements Lookup Patient Rx History by Last Name or First Name and DOB and match by Last Name, First Name and DOB |
| Patient Predict Elements Lookup by Machine Learning read Address or by Last Name, or First Name, Phone or DOB and match by Last Name, First Name and DOB |
| Patient Predict Restricted Match Reverse lookup using Phone and match by First Name and DOB |
| Patient Predict Restricted Match reverse lookup using Address and match by First Name and DOB |
| Patient Predict Restricted Match Reverse lookup using Phone and match by Last Name and DOB |
| Patient Predict Restricted Match reverse lookup using Address and match by Last Name and DOB |
| Patient Predict Restricted Match Reverse lookup using Phone and match by Last Name and First Name |
| Patient Predict Restricted Match reverse lookup using Address and match by Last Name and First Name |
| Patient Predict Restricted Match reverse lookup using Partial Address and match by Last Name and DOB |
| Patient Predict Restricted Match reverse lookup using Partial Address and match by Last Name and First Name |
| Patient Predict Restricted Match reverse lookup using Partial Address and match by First Name and DOB |
| Patient Predict Elements Restricted Match Reverse lookup using Phone and match by First Name and DOB |

TABLE 1-continued

| Patient Predict Elements Restricted Match reverse lookup using Address and match by First Name and DOB |
| --- |

Control then obtains a document scan candidate field value at 1312. For example, control may analyze prior document scan data, rescan the document, etc., to determine whether the document includes any fields that may be similar to the predicted missing field value. The document scan candidate field value may be considered to include a string, date, number, etc. from the scanned document, which may be compared with the predicted missing field value to determine whether the predicted missing field value is actually present in the document (but may have been scanned incorrectly, missed in the initial scan analysis, etc.).

Control then determines a field type for the match check at 1316, such as a first name field type, a last name field type, a date field type, etc. If control determines at 1320 that the field type is a name (such as a patient first name, a patient last name, a prescriber name, etc.), control proceeds to 1324 to perform a name field fuzzy match algorithm (e.g., to match a name string of the predicted missing field value to a name string of the document scan candidate field value). An example name field fuzzy match algorithm is described further below with reference to FIG. 14.

Once control performs the name fuzzy match algorithm at 1324, control returns the result of the field match check algorithm at 1340. For example, if control determines that a name string of the predicted field value matches a name string of the document scan candidate field value (e.g., where the document includes a patient name that is sufficiently close to a missing patient name on the initial scan, as predicted based on other scanned document information associated with the patient name), control may return a result that the document includes a matching name. If control determines at 1324 that the document does not include a name fuzzy match based on the algorithm, control may return a result of no successful match, or that the predicted name is not present in the scanned document.

If control determines at 1320 that the field type is not a name field type, control proceeds to 1328 to determine whether the field type is a date field type. For example, control may determine whether at least one of the predicted missing field value and the document scan candidate field value have a date field format type.

If the field type is a date format at 1328, control proceeds to 1332 to perform a date matching algorithm. For example, control may determine whether a specific date of the predicted missing field value (such as a patient date of birth) matches a same (or sufficiently similar) date of the document scan candidate field value.

The dates may be in different formats in the predicted missing field value and the document scan candidate field value, and the date matching algorithm may account for possible differences in date formats. An example date matching algorithm is described further below with reference to FIG. 15.

After control completes the date matching algorithm at 1332, control proceeds to 1340 to return the result of the field match check algorithm. For example, if control determines that a date of the predicted missing field value is the same or sufficiently similar as a date of the document scan candidate field value, control may return a successful match, indicating that an expected or predicted date was actually present in the document even if missed, or in a different format, during the original scan. If control determines that there is not a date match, control may return an unsuccessful match at 1340.

If control determines at 1328 that the filed type of the missing predicted missing field value or the document scan candidate value is not a date, control proceeds to 1336 to perform a general fuzzy match algorithm between the predicted missing field value and the document scan candidate field value. For example, if control determines that the field type is not a name string, or a date format, control may use other suitable matching algorithms (which may or may not include fuzz match algorithms) to determine whether the predicted missing field value is actually present in the document. Control then returns the result of the field match check algorithm based on the general match algorithm at 1340.

FIG. 14 is a flowchart depicting an example process for determining whether a document scan name field matches a predicted missing name field value. At 1404, control begins by reciting a name field match check request. For example, a general control process may request to determine whether a predicted name string matches a document scan candidate name (such as at 1324 in FIG. 13), in order to determine whether a missing name (e.g., patient first name, patient last name, prescriber name, etc.) is actually present in a document but may have been missed in an original scan, scanned incorrectly, entered with a typographical error by an original document drafter, etc.

At 1408, control obtains a predicted missing name field value, and at 1412 control obtains a document scan candidate name field value. Control then calculates a Levenshtein distance (sometimes referred to as an edit distance) between the predicted missing name field value (e.g., a first name string) and the document scan candidate name field value (e.g., a second name string), at 1416.

A Levenshtein distance is a string metric for measuring the difference between two sequences. In various implementations, the Levenshtein distance between two words may be considered as the minimum number of single-character edits (e.g., insertions, deletions or substitutions) required to change one word into the other.

An example Levenshtein distance between two strings of length and respectively) may be given by where $$lev(a,b) = \begin{cases} |a| & \text{if } |b| = 0, \\ |b| & \text{if } |a| = 0, \\ lev(\text{tail}(a), \text{tail}(b)) & \text{if } a[0] = b[0], \\ 1 + \min\begin{cases} lev(\text{tail}(a), b) \\ lev(a, \text{tail}(b)) \\ lev(\text{tail}(a), \text{tail}(b)) \end{cases} & \text{otherwise,} \end{cases}$$

where the tail of some string x is a string of all but the first character of x, and x[n] is the $n^{th}$ character of the string x, counting from 0. The first element in the minimum may correspond to deletion (from a to b), the second to insertion and the third to replacement.

At 1420, control calculates a Jaro-Winkler distance between the predicted missing name field value and the document scan candidate name field value. The Jaro-Winkler distance is a string metric, which may be considered as another algorithm for measuring an edit distance between two sequences.

The Jaro-Winkler distance is a string comparator measure that gives values of partial agreement between two strings. The string comparator accounts for length of strings, and partially accounts for typical human errors made in alphanumeric strings. For example, a Jaro-Winkler distance between "shackleford" and "shackelford" may be equal to 2 (e.g., before normalization).

The Jaro-Winkler distance uses a prefix scale p which gives more favorable ratings to strings that match from the beginning for a set prefix length l. An Jaro similarity $sim_j$ of two given strings $s_1$ and $s_2$ is $$sim_j = \begin{cases} 0 & \text{if } m = 0 \\ \frac{1}{3}\left(\frac{m}{|s_1|} + \frac{m}{|s_2|} + \frac{m-t}{m}\right) & \text{otherwise} \end{cases}$$

Where $|s_i|$ is the length of the string $s_i$, m is the number of matching characters, and t is the number of transpositions. The higher the Jaro-Winkler distance for two strings is, the more similar the strings are. The score is normalized such that 1 means an exact match and 0 means there is no similarity.

At 1424, control calculates a weighted average of the Levenshtein distance and the Jaro-Winkler distance. For example, the calculated Levenshtein and Jaro-Winkler may be combined with equal weights, one distance may be weighted more than the other, etc. The weights may be determined and adjusted as desired, in order to improve the accuracy of identifying correct matches between the predicted missing name field value and the document scan candidate name field value. Although FIG. 14 illustrates a weighted average of Jaro-Winkler and Levenshtein distances, other example embodiments may use only one of the Jaro-Winkler and Levenshtein distances, other types of fuzzy matching algorithms, etc.

At 1428, control compares the weighted average to a specified matching threshold value (e.g., a similarity score that sufficiently indicates a correct match between the predicted missing name field value and the document scan candidate name field value based on the weighted Levenshtein distance and Jaro-Winkler distance). Example thresholds may include, but are not limited to, 0.75 (where 0 is no match at all and 1 is an exact match), 0.85, 0.9, etc.

If the weighted average is greater than the threshold at 1432, control returns a successful result for the name field match. If the weighted average is less than the threshold at 1432, control returns an unsuccessful match result indicating that the predicted missing name value is not sufficiently similar to the document scan candidate name field value.

Table 2 below illustrates examples of Jaro-Winkler distance and Levenshtein distance for comparing various String 1 and String 2 values that have partial overlap. The distances in Table 2 may be normalized to a scale of 0 to 100 (similar to a normalization scale of 0 to 1).

TABLE 2

| String 1 | String 2 | Jaro-Winkler | Levenshtein |
|---|---|---|---|
| Dunningham | Cunnigham | 89 | 80 |
| Abroms | Abrams | 92 | 83 |
| Lampley | Campley | 90 | 86 |
| Marhta | Martha | 96 | 67 |
| Jonathon | Jonathan | 95 | 88 |
| Jeraldine | Geraldine | 92 | 89 |

FIG. 15 is a flowchart depicting an example process for determining whether a document scan date field matches a predicted missing date field value. At 1504, control begins by receiving a date field match check request. Control the obtains a predicted missing date field value at 1508.

At 1512, control obtains a document scan candidate date field values. Control obtains multiple date format entries at 1516. for example, dates may be presented in various formats in different documents, e.g., listing days, months and years in different orders, listing years with full or partial values, writing out months or using numbers, etc.

Control may obtain a list of various formats to check for the predicted missing date field value and/or document scan candidate date field value. Table 3 below provides an example list of various date formats, although other embodiments may include other example formats.

TABLE 3

| |
|---|
| Mon dd, yyyy |
| mm/dd/yyyy |
| mon dd, yyyy |
| mmddyyyy |
| ddmmyyyy |
| MONTH DD yyyy |
| MONTH DD, yyyy |
| mmddyyyy |
| mmddyy |

At 1520, control selects a first date format entry (such as one of the example format entries in Table 3 above). Control then determines whether the document scan candidate date field value matches the first date format entry at 1524. For example, control may determine whether the document scan candidate date field value has the same format as the selected date format energy obtained from, e.g., a list or database of possible date formats.

If the date format does not match at 1528, control proceeds to 1532 to determine whether there are additional date formats remaining in the list, database, etc. If so, control selects a next date format entry at 1540, and returns to 1524 to determine whether the document scan candidate date field value matches the first date format entry.

If control determines at 1532 that there are not additional date formats remaining, control proceeds to 1536 to return a result that the date field did not have a matched result (e.g., control was not able to match the predicted missing date field value to a document scan candidate date field value).

Once control determines at 1528 that the document scan candidate date field matches the selected date format entry, control proceeds to 1544 to compare the document scan candidate date field to the predicted missing date field value. For example, once a match is determined at 1528, control may be able to identify a specific date field in the document, and control can compare the document date field to the predicted missing date field value, even if the two dates use different formats.

If control determines at 1548 that the date file values do not match, control proceeds to 1536 to return a date field match unsuccessful result. If control determines at 1548 that the date field values do match, control returns a success result of the date field matching at 1552.

CONCLUSION

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. In the written description and claims, one or more steps within a method may be executed in a different order (or concurrently) without altering the principles of the present disclosure. Similarly, one or more instructions stored in a non-transitory computer-readable medium may be executed in different order (or concurrently) without altering the principles of the present disclosure. Unless indicated otherwise, numbering or other labeling of instructions or method steps is done for convenient reference, not to indicate a fixed order.

Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements.

The phrase "at least one of A, B, and C" should be construed to mean a logical (A OR B OR C), using a non-exclusive logical OR, and should not be construed to mean "at least one of A, at least one of B, and at least one of C." The term "set" does not necessarily exclude the empty set. The term "non-empty set" may be used to indicate exclusion of the empty set. The term "subset" does not necessarily require a proper subset. In other words, a first subset of a first set may be coextensive with (equal to) the first set.

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A.

In this application, including the definitions below, the term "module" or the term "controller" may be replaced with the term "circuit." The term "module" may refer to, be part of, or include processor hardware (shared, dedicated, or group) that executes code and memory hardware (shared, dedicated, or group) that stores code executed by the processor hardware.

The module may include one or more interface circuits. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2016 (also known as the WIFI wireless networking standard) and IEEE Standard 802.3-2015 (also known as the ETHERNET wired networking standard). Examples of a WPAN are IEEE Standard 802.15.4 (including the ZIGBEE standard from the ZigBee Alliance) and, from the Bluetooth Special Interest Group (SIG), the BLUETOOTH wireless networking standard (including Core Specification versions 3.0, 4.0, 4.1, 4.2, 5.0, and 5.1 from the Bluetooth SIG).

The module may communicate with other modules using the interface circuit(s). Although the module may be depicted in the present disclosure as logically communicating directly with other modules, in various implementations the module may actually communicate via a communications system. The communications system includes physical and/or virtual networking equipment such as hubs, switches, routers, and gateways. In some implementations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various implementations, the functionality of the module may be distributed among multiple modules that are connected via the communications system. For example, multiple modules may implement the same functionality distributed by a load balancing system. In a further example, the functionality of the module may be split between a server (also known as remote, or cloud) module and a client (or, user) module. For example, the client module may include a native or web application executing on a client device and in network communication with the server module.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of a non-transitory computer-readable medium are nonvolatile memory devices (such as a flash memory device, an erasable programmable read-only memory device, or a mask read-only memory device), volatile memory devices (such as a static random access memory device or a dynamic random access memory device), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. Such apparatuses and methods may be described as computerized apparatuses and computerized methods. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, JavaScript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

What is claimed is:

1. A computer system for automated correction of missing or incorrect data fields in images of received facsimile transmissions, the computer system comprising:

memory hardware configured to store a machine learning model, a record database, structured classification data, multiple machine learning models, and computer-executable instructions, wherein the record database includes multiple patient data structures and multiple prescriber data structures, the structured classification data includes multiple entity classification types, and each of the multiple machine learning models is associated with a different one of the multiple entity classification types; and processor hardware configured to execute the instructions, wherein the instructions include:

scanning a database entity to generate structured scan data specific to the database entity, wherein the database entity includes at least one image of a prescription fill request document received via facsimile transmission, and scanning the database entity includes performing automated optical character recognition on the at least one image of the prescription fill request document received via facsimile transmission;

analyzing the database entity to identify one of the multiple entity classification types corresponding to the database entity, wherein different types of fax metadata are associated with different document classifications, and a mapping of the fax metadata is stored in a list for classification of prescription fill request documents received via facsimile transmission;

selecting one of the multiple machine learning models according to the identified one of the multiple entity classification types, the multiple machine learning models including a machine learning model trained to process optical character recognition (OCR) data for prescription fill request documents that include a cover page;

generating a feature vector input according to the structured scan data;

processing, by the selected one of the multiple machine learning models associated with the classification of the database entity, the feature vector input to generate an entity field output including multiple identified entity fields and values of the identified entity fields;

determining whether the entity field output includes at least one missing field value;

transmitting the database entity to a prescription fill processing module for automated processing of a prescription fill specified by the database entity, in response to determining that the entity field output does not include at least one missing field value;

for each database entity transmitted to the prescription fill processing module, automatically controlling an automated dispensing device by:

identifying a prescription drug associated with the respective database entity;

controlling movement of a set of containers relative to an automated dispensing device without operator intervention;

automatically dispensing, via the automated dispensing device, the prescription drug into a container of the set of containers;

imaging the container by an imaging device to automatically measure a fill height of pharmaceuticals in the container based on processing an obtained image; and securing the container with a cap by a cap device to seal pharmaceuticals in the container; and in response to determining that the entity field output includes at least one missing field value:

accessing the record database to identify a predicted value for the at least one missing field value in the entity field output, wherein the predicted value is stored in association with at least one entity field value of the entity field output in at least one of the multiple patient data structures and the multiple prescriber data structures of the record database;

performing an OCR scan of a prescription fill request document of the database entity to locate a predicted patient name in the prescription fill request document, wherein the predicted value for the at least one missing field value in the entity field output includes the predicted patient name, and wherein the OCR scan to locate the predicted patient name outputs a scanned name string;

comparing a predicted name string of the predicted value to the scanned name string of the structured scan data to determine at least one of a Levenshtein distance and a Jaro-Winkler distance between the predicted name string and the scanned name string; and in response to determining that a similarity score between the predicted name string and the scanned name string according to the at least one of the Levenshtein distance and the Jaro-Winkler distance is greater than a specified similarity threshold, transmitting the database entity to the prescription fill processing module for automated processing of the prescription fill specified by the database entity.

2. The system of claim 1, wherein:

comparing the predicted name string to the scanned name string includes determining both of the Levenshtein distance and the Jaro-Winkler distance between the predicted name string and the scanned name string; and the similarity score between the predicted name string and the scanned name string is determined according to both the Levenshtein distance and the Jaro-Winkler distance between the predicted name string and the scanned name string.

3. The system of claim 2, wherein the similarity score between the predicted name string and the scanned name string is determined according to both the Levenshtein distance and the Jaro-Winkler distance.

4. The system of claim 1, wherein:

the memory hardware is configured to store historical feature vector inputs, and the historical feature vector inputs include historical data structures specific to multiple historical database entities; and the instructions include training the multiple machine learning models with the historical feature vector inputs to generate an entity field output, wherein the entity field output includes multiple identified entity fields and values of the identified entity fields.

5. The system of claim 1, wherein the instructions include:

determining whether the predicted value for the at least one missing field value in the entity field output includes a predicted date field;

comparing the predicted date field to a scanned date field of the structured scan data; and in response to determining that the predicted date field to a scanned date field of the structured scan data, transmitting the database entity including the predicted date field to the prescription fill processing module.

6. The system of claim 5, wherein:

the memory hardware is configured to store multiple date field formats; and comparing the predicted date field to the scanned date field includes, for each of the multiple date field formats, determining whether the structured scan data includes a date value having the date field format.

7. The system of claim 1, wherein obtaining the database entity includes receiving a prescription fill request document via facsimile transmission.

8. The system of claim 1, wherein scanning the database entity includes performing automated optical character recognition on the database entity.

9. The system of claim 1, wherein the instructions include:

determining whether the predicted value for the at least one missing field value in the entity field output includes a predicted date field;

comparing the predicted date field to a scanned date field of the structured scan data; and in response to determining that the predicted date field to a scanned date field of the structured scan data, transmitting the database entity including the predicted date field to the prescription fill processing module;

wherein the memory hardware is configured to store multiple date field formats; and wherein obtaining the database entity includes receiving a prescription fill request document via facsimile transmission.

10. The system of claim 9, wherein comparing the predicted date field to the scanned date field includes, for each of the multiple date field formats, determining whether the structured scan data includes a date value having the date field format.

11. A method for automated correction of missing or incorrect data fields in images of received facsimile transmissions, the method comprising:

scanning a database entity to generate structured scan data specific to the database entity, wherein the database entity includes at least one image of a prescription fill request document received via facsimile transmission, and scanning the database entity includes performing automated optical character recognition on the at least one image of the prescription fill request document received via facsimile transmission;

generating a feature vector input according to the structured scan data;

analyzing the database entity, according to structured classification data, to identify one of multiple entity classification types corresponding to the database entity, wherein the structured classification data includes multiple entity classification types, and each of multiple machine learning models is associated with a different one of the multiple entity classification types, wherein different types of fax metadata are associated with different document classifications, and a mapping of the fax metadata is stored in a list for classification of prescription fill request documents received via facsimile transmission;

selecting one of the multiple machine learning models according to the identified one of the multiple entity classification types, the multiple machine learning models including a machine learning model trained to process optical character recognition (OCR) data for prescription fill request documents that include a cover page;

processing, by the selected one of the multiple machine learning models associated with the classification of the database entity, the feature vector input to generate an entity field output including multiple identified entity fields and values of the identified entity fields;

determining whether the entity field output includes at least one missing field value;

transmitting the database entity to a prescription fill processing module for automated processing of a prescription fill specified by the database entity, in response to determining that the entity field output does not include at least one missing field value;

for each database entity transmitted to the prescription fill processing module, automatically controlling an automated dispensing device by:

identifying a prescription drug associated with the respective database entity;

controlling movement of a set of containers relative to an automated dispensing device without operator intervention;

automatically dispensing, via the automated dispensing device, the prescription drug into a container of the set of containers;

imaging the container by an imaging device to automatically measure a fill height of pharmaceuticals in the container based on processing an obtained image; and securing the container with a cap by a cap device to seal pharmaceuticals in the container; and in response to determining that the entity field output includes at least one missing field value:

accessing a record database to identify a predicted value for the missing field value in the entity field output, wherein the record database includes multiple patient data structures and multiple prescriber data structures, and wherein the predicted value is stored in association with at least one entity field value of the entity field output in at least one of the multiple patient data structures and the multiple prescriber data structures of the record database;

performing an OCR scan of a prescription fill request document of the database entity to locate a predicted patient name in the prescription fill request document, wherein the predicted value for the at least one missing field value in the entity field output includes the predicted patient name, and wherein the OCR scan to locate the predicted patient name outputs a scanned name string;

comparing a predicted name string of the predicted value to a scanned name string of the structured scan data to determine at least one of a Levenshtein distance and a Jaro-Winkler distance between the predicted name string and the scanned name string; and in response to determining that a similarity score between the predicted name string and the scanned name string according to the at least one of the Levenshtein distance and the Jaro-Winkler distance is greater than a specified similarity threshold, transmitting the database entity to the prescription fill processing module for automated processing of the prescription fill specified by the database entity.

12. The method of claim 11, wherein:

comparing the predicted name string to the scanned name string includes determining both of the Levenshtein distance and the Jaro-Winkler distance between the predicted name string and the scanned name string; and the similarity score between the predicted name string and the scanned name string is determined according to both the Levenshtein distance and the Jaro-Winkler distance between the predicted name string and the scanned name string.

13. The method of claim 12, wherein the similarity score between the predicted name string and the scanned name string is determined according to both the Levenshtein distance and the Jaro-Winkler distance.

14. The method of claim 11, further comprising training the multiple machine learning models with historical feature vector inputs to generate an entity field output, wherein the historical feature vector inputs include historical data structures specific to multiple historical database entities, and the entity field output includes multiple identified entity fields and values of the identified entity fields.

15. The method of claim 11, further comprising:

determining whether the predicted value for the missing field value in the entity field output includes a predicted date field;

comparing the predicted date field to a scanned date field of the structured scan data; and in response to determining that the predicted date field to a scanned date field of the structured scan data, transmitting the database entity including the predicted date field to the prescription fill processing module.

16. The method of claim 15, wherein comparing the predicted date field to the scanned date field includes, for each of multiple date field formats, determining whether the structured scan data includes a date value having the date field format.

17. The method of claim 11, wherein obtaining the database entity includes receiving a prescription fill request document via facsimile transmission.

18. The method of claim 11, wherein scanning the database entity includes performing automated optical character recognition on the database entity.

19. The method of claim 11, further comprising:

determining whether the predicted value for the missing field value in the entity field output includes a predicted date field;

comparing the predicted date field to a scanned date field of the structured scan data; and in response to determining that the predicted date field to a scanned date field of the structured scan data, transmitting the database entity including the predicted date field to the prescription fill processing module.

20. The method of claim 19, wherein comparing the predicted date field to the scanned date field includes, for each of multiple date field formats, determining whether the structured scan data includes a date value having the date field format.

* * * * *